(12) United States Patent
Hamada

(10) Patent No.: US 7,883,522 B2
(45) Date of Patent: Feb. 8, 2011

(54) MINIMAL ACCESS LUMBAR DISKECTOMY INSTRUMENTATION AND METHOD

(75) Inventor: James S. Hamada, Torrance, CA (US)

(73) Assignee: K2M, Inc., Leesburg, VA (US)

(*) Notice: Subject to any disclaimer, the term of this patent is extended or adjusted under 35 U.S.C. 154(b) by 1042 days.

(21) Appl. No.: 11/165,295

(22) Filed: Jun. 22, 2005

(65) Prior Publication Data

US 2005/0240209 A1 Oct. 27, 2005

Related U.S. Application Data

(60) Continuation-in-part of application No. 11/001,628, filed on Nov. 30, 2004, now Pat. No. 7,173,240, which is a division of application No. 10/280,624, filed on Oct. 25, 2002, now Pat. No. 6,849,064.

(51) Int. Cl.
*A61B 17/32* (2006.01)

(52) U.S. Cl. .................. 606/174; 606/208; 604/164.01

(58) Field of Classification Search ................ 606/144, 606/147, 151, 171, 174, 180, 205–211; 604/164.01–164.06, 164.11, 164.12, 264
See application file for complete search history.

(56) References Cited

U.S. PATENT DOCUMENTS

| | | | |
|---|---|---|---|
| 1,613,141 A | 1/1927 | Stein | |
| 2,693,795 A | 11/1954 | Grieshaber | |
| 3,129,706 A | 4/1964 | Reynolds | |
| 3,227,156 A | 1/1966 | Gauthier | |
| 3,724,449 A | 4/1973 | Gauthier | |
| 3,750,652 A * | 8/1973 | Sherwin | ...................... 606/90 |
| 4,263,899 A | 4/1981 | Burgin | |

(Continued)

FOREIGN PATENT DOCUMENTS

DE 201 109 12/1907

(Continued)

OTHER PUBLICATIONS

International Search Report for European Application No. EP 1 949 860, as published on Oct. 1, 2008.

(Continued)

*Primary Examiner*—Kevin T Truong
(74) *Attorney, Agent, or Firm*—Carter, DeLuca, Farrell & Schmidt, LLP

(57) ABSTRACT

A minimal incision maximal access system allows for maximum desirable exposure along with maximum access to the operative field utilizing a minimum incision as small as the METRx and Endius systems. Instead of multiple insertions of dilating tubes the design is a streamlined single entry device to avoid repetitive skin surface entry. The system offers the capability to expand to optimum exposure size for the surgery utilizing hinged bi-hemispherical or oval working tubes applied over an introducer obturator which is controllably dilated to slowly separate muscle tissue. Deeper end working and visualization areas with maximum proximal access and work dimensions are provided to makes the operative procedure safer in application and shorten the surgeons's learning curve because it most closely approximates the ability to use open microdiskectomy techniques. a dual frame system enables full or partial spreading of a working tube set, while an open frame facilitates a four point retraction system.

10 Claims, 16 Drawing Sheets

U.S. PATENT DOCUMENTS

| | | | |
|---|---|---|---|
| 4,300,541 | A | 11/1981 | Burgin |
| 4,545,374 | A | 10/1985 | Jacobson |
| 4,747,394 | A | 5/1988 | Watanabe |
| 4,852,552 | A | 8/1989 | Chaux |
| 4,924,857 | A | 5/1990 | Mahmoodian |
| 4,926,849 | A | 5/1990 | Downey |
| 4,989,587 | A | 2/1991 | Farley |
| 4,991,566 | A | 2/1991 | Shulman |
| 5,503,617 | A | 4/1996 | Jako |
| 5,505,690 | A | 4/1996 | Patton et al. |
| 5,529,571 | A | 6/1996 | Daniel |
| 5,582,577 | A | 12/1996 | Lund |
| 5,616,117 | A | 4/1997 | Dinkler et al. |
| 5,667,520 | A | 9/1997 | Bonutti |
| 5,707,359 | A | 1/1998 | Bufalini |
| 5,707,362 | A | 1/1998 | Yoon |
| 5,776,054 | A | 7/1998 | Bobra |
| 5,785,648 | A * | 7/1998 | Min ............... 600/206 |
| 5,813,978 | A | 9/1998 | Jako |
| 5,885,210 | A | 3/1999 | Cox |
| 5,902,233 | A | 5/1999 | Farley et al. |
| 5,928,139 | A | 7/1999 | Koros |
| 5,931,777 | A | 8/1999 | Sava |
| 5,944,658 | A | 8/1999 | Koros et al. |
| 5,967,972 | A | 10/1999 | Santilli et al. |
| 6,074,343 | A * | 6/2000 | Nathanson et al. ......... 600/214 |
| 6,224,545 | B1 | 5/2001 | Cocchia et al. |
| 6,241,659 | B1 | 6/2001 | Bookwalter et al. |
| 6,524,320 | B2 | 2/2003 | DiPoto |
| 6,530,926 | B1 | 3/2003 | Davison |
| 6,616,605 | B2 | 9/2003 | Wright |
| 6,652,553 | B2 | 11/2003 | Davison et al. |
| 6,688,195 | B1 | 2/2004 | Hsien |
| 6,712,795 | B1 | 3/2004 | Cohen |
| 6,743,206 | B1 | 6/2004 | Smith et al. |
| 6,761,725 | B1 * | 7/2004 | Grayzel et al. ............. 606/174 |
| 6,767,349 | B2 * | 7/2004 | Ouchi ...................... 606/205 |
| 6,767,355 | B2 | 7/2004 | Frova et al. |
| 6,796,422 | B1 | 9/2004 | Lu |
| 6,849,064 | B2 | 2/2005 | Hamada |
| 6,869,398 | B2 | 3/2005 | Obenchain et al. |
| 6,945,933 | B2 | 9/2005 | Branch et al. |
| 7,056,329 | B2 | 6/2006 | Kerr |
| 2003/0004401 | A1 | 1/2003 | Ball |
| 2003/0191371 | A1 | 10/2003 | Smith et al. |
| 2004/0024291 | A1 | 2/2004 | Zinkel |
| 2004/0093000 | A1 | 5/2004 | Kerr |
| 2004/0176665 | A1 | 9/2004 | Branch et al. |
| 2004/0215199 | A1 | 10/2004 | Zinkel |
| 2004/0230100 | A1 | 11/2004 | Shluzas |
| 2004/0230191 | A1 | 11/2004 | Frey et al. |
| 2005/0070765 | A1 | 3/2005 | Abdelgany et al. |
| 2005/0080320 | A1 | 4/2005 | Lee et al. |
| 2005/0159650 | A1 | 7/2005 | Raymond et al. |
| 2005/0159651 | A1 | 7/2005 | Raymond et al. |
| 2005/0215866 | A1 | 9/2005 | Kim |
| 2005/0234304 | A1 | 10/2005 | Dewey et al. |
| 2005/0277812 | A1 | 12/2005 | Myles |
| 2006/0052812 | A1 | 3/2006 | Winer |
| 2006/0178693 | A1 | 8/2006 | Hamada |
| 2007/0055247 | A1 | 3/2007 | Jahng |

FOREIGN PATENT DOCUMENTS

| | | |
|---|---|---|
| DE | 28 01 696 | 7/1979 |
| EP | 0 455 282 | 11/1991 |
| EP | 1632185 | 3/2006 |
| WO | WO 02/09801 | 2/2002 |
| WO | WO 2005/094695 | 10/2005 |

OTHER PUBLICATIONS

About Endius/Corporate Overview, (Internet Reference, 2002).

Aldrich, "Posterolateral microdiscectomy for cervical monoradiculopathy caused by posterolateral soft cervical disc dequestration", *J. Neurosurg.* 72:370-377 (1990).

Aronson, "The management of soft cervical disc protrusions using the Smith-Robinson approach", *Clinical Neurosurgery* 20:253-258 (1973).

Caspar, "A new surgical procedure for lumbar disc herniation causing less tissue damage through a microsurgical approach", *Adv Neurosurg* 4:72-80 (1977).

Cloward, "The Anterior Approach for Removal of Ruptured Cervical Disks", Presented at the meeting of the Harvey Cushing Society, Washington, DC, Apr. 22, 1958, pp. 602-617.

Fessler, et al., "Minimally Invasive Cervical Microendoscopic Foraminotomy: An Initial Clinical Experience", *Neurosurgery* 51(2):2-10 (2002).

Fessler, et al., "A minimally invasive technique for decompression of the lumbar spine", *Spine* 27:432-438 (2002).

Foley, et al., "Microendoscopic Discectomy", *Techniques in Neurosurgery* 3(4):301-307 (1997).

Henderson, et al., "Posterior-Lateral Foraminotomy as an Exclusive Operative Technique for Cervical Radiculopathy: A Review of 846 consecutively Operated Cases", *Neurosurgery*, 13(5): 504-521 (1983).

Hermantin, et al., "A Prospective, Randomized Study Comparing the Results of Open discectomy with Those of Video-Assisted Arthroscopic Microdiscectomy", *The Journal of Bone and Joint Surgery* 81A(7):958-965 (1999).

Kawaguchi, et al., "Back Muscle Injury After Posterior Lumbar Spine Surgery", *Spine*, 21(8):941-944 (1996).

Lin, et al., "Posterior Lumbar Interbody Fusion", *Clinical Orthopedics and Related Research*, No. 180, pp. 154-168 (1983).

Lin, "Posterior Lumbar Interbody Fusion Technique: Complications and Pitfalls", *PLIF Complications and Pitfalls*, No. 193, pp. 90-102 (1985).

Malis, "Instrumentation and Techniques in Microsurgery", *Clinical Neurosurgery*, 26:626-636 (1979).

Rantanen, et al., "The Lumbar Multifidus Muscle Five Years After Surgery for a Lumbar Intervertebral Disc Herniation", *Spine*, 18(5):268-274 (1993).

Roh, et al., "Endoscopic Foraminotomy Using MED System in Cadaveric Specimens", *Spine*, 25(2):260-264 (2000).

Sihvonen, et al., "Local denervation atrophy of paraspinal muscles in postoperative failed back syndrome", *Spine* 18:575-581 (1993).

Styf, et al., "The Effects of External Compression by Three Different Retractors on Pressure in the Erector Spine Muscles During and After Posterior Lumbar Spine Surgery in Humans", *Spine*, 23(3):354-358 (1998).

Tsai, et al., "Microscopic Laminotomies for Degenerative Lumbar Spinal Stenosis", *Journal of Spinal disorders*, 11(5):389-394 (1998).

Weber et al, "Posterior surgical approach to the lumbar spine and its effect on the multifidus muscle", *Spine* 22:1765-1772 (1992).

Weiner, et al., "Microdecompression for Lumbar Spinal Canal Stenosis", *Spine*, 24(21):2268-2272 (1999).

Endius: The Pioneer of Endoscopic Spine Fusion Atavi System: Endoscopic Posterolateral Fusion (Internet Reference).

The Supplementary European Search Report for Application No. EP 03 80 9631 dated Mar. 17, 2009.

* cited by examiner

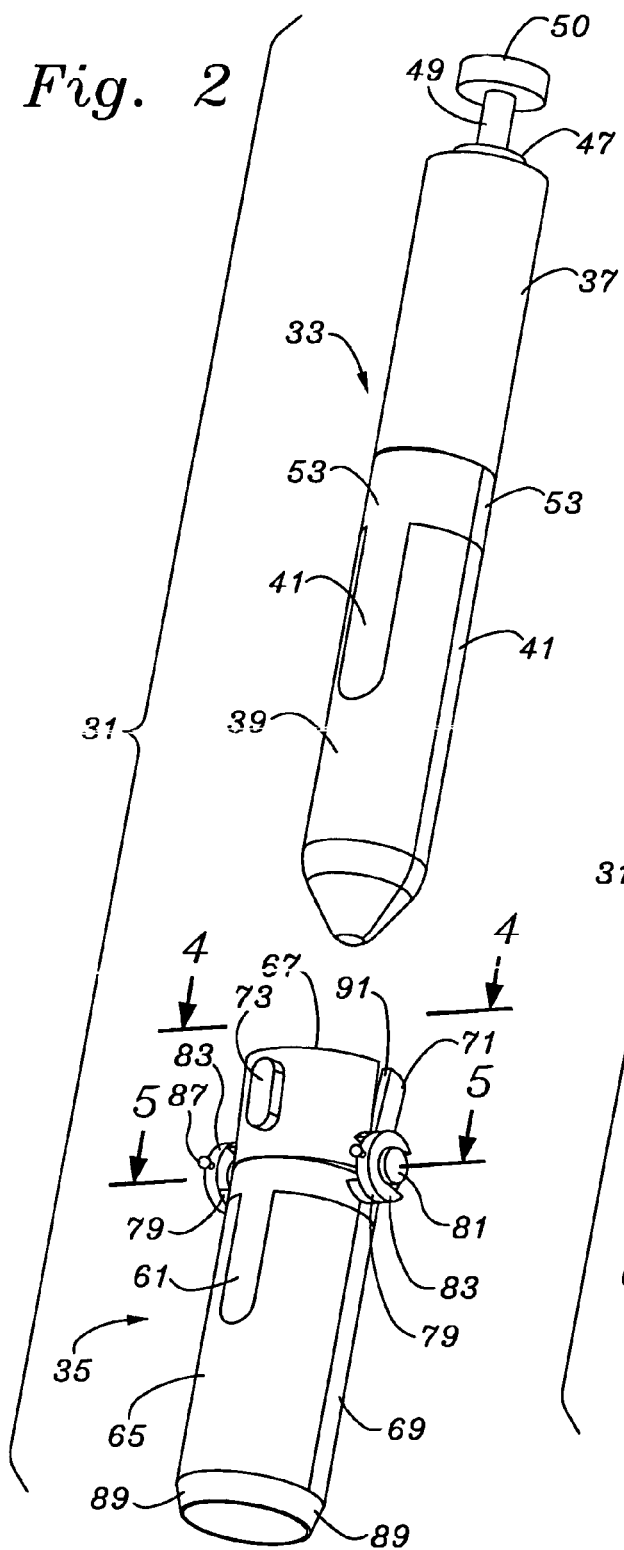
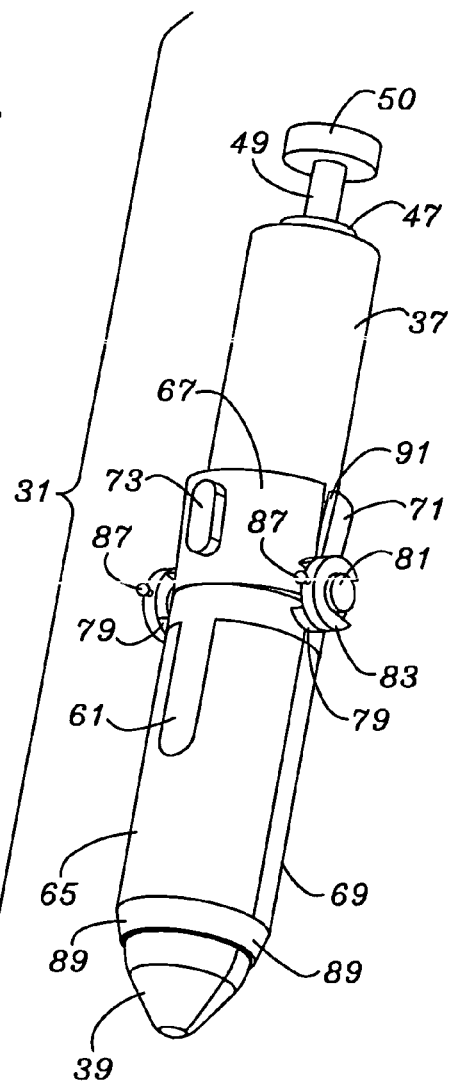

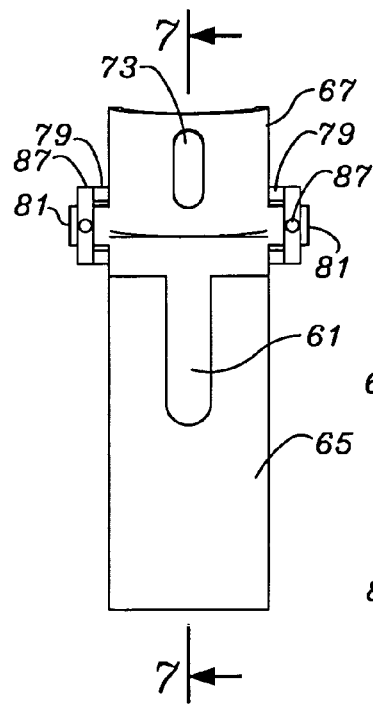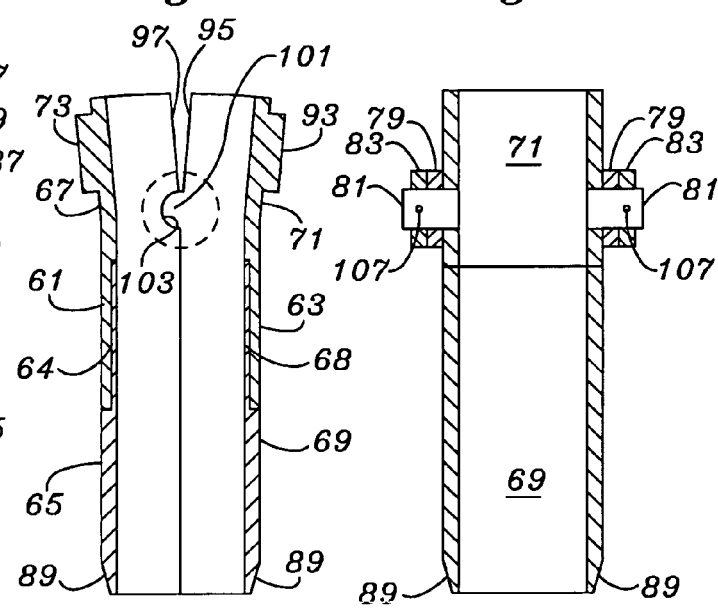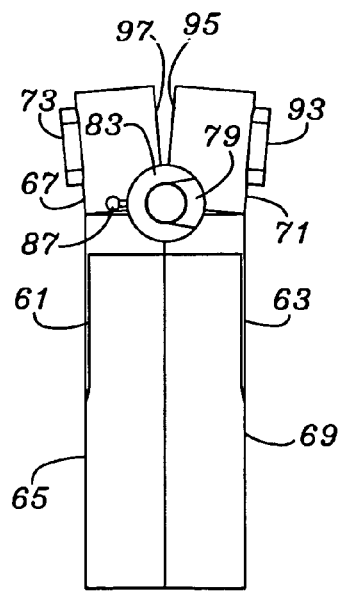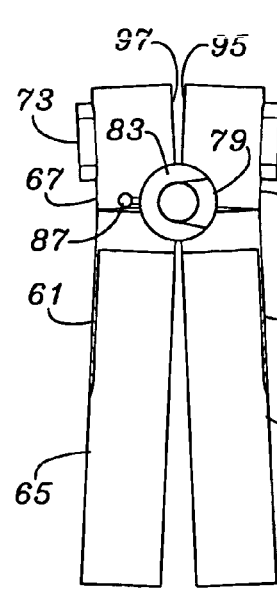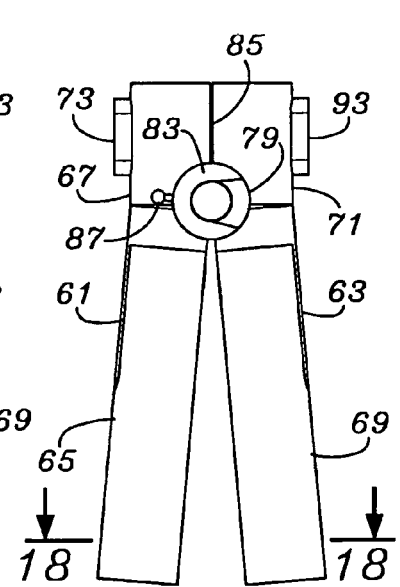

Fig. 17
Fig. 18
Fig. 15
Fig. 16
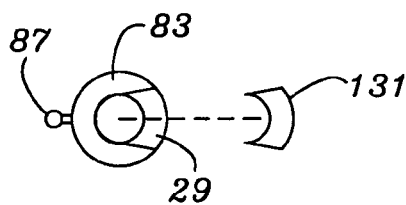
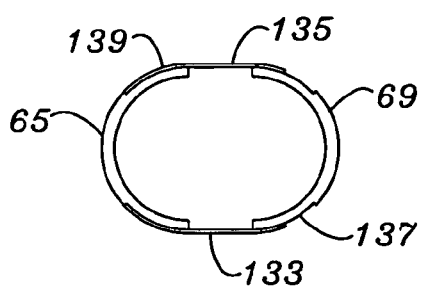
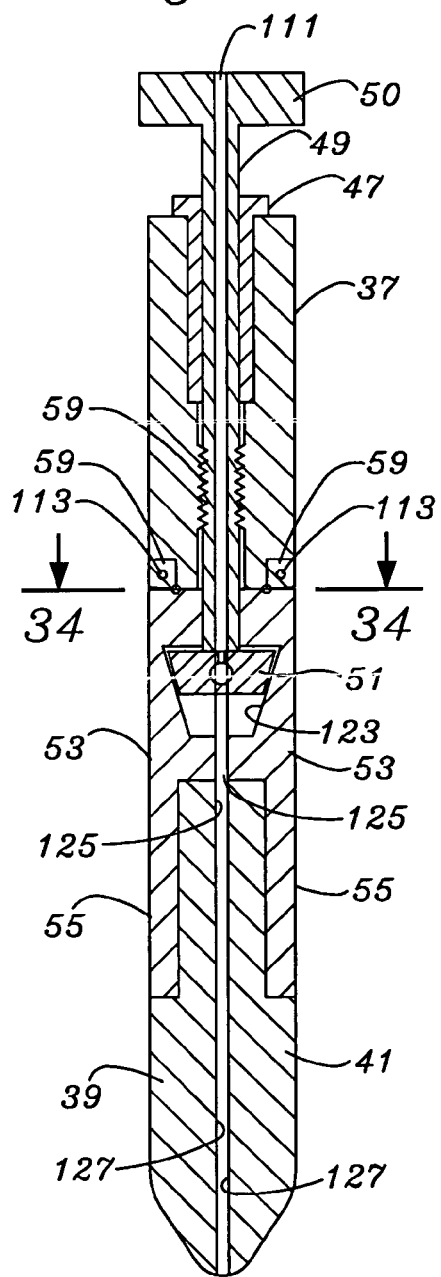
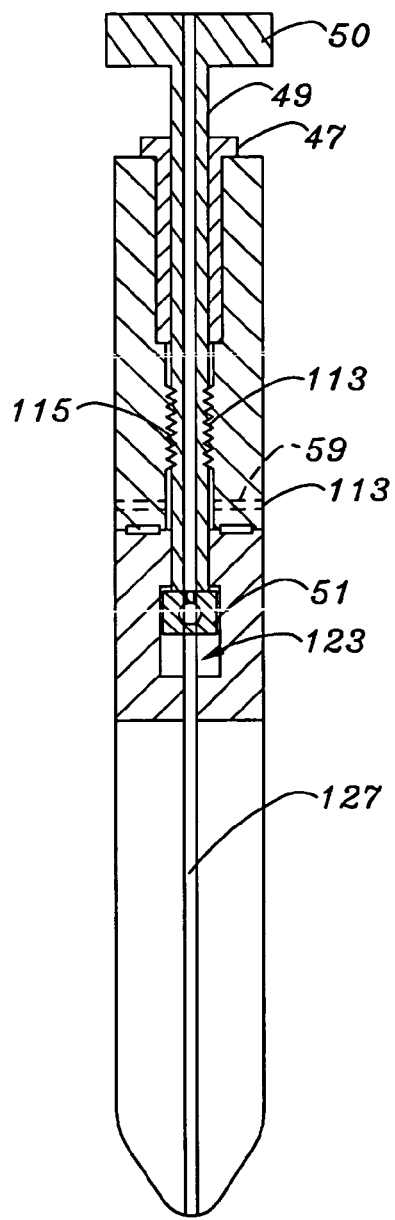

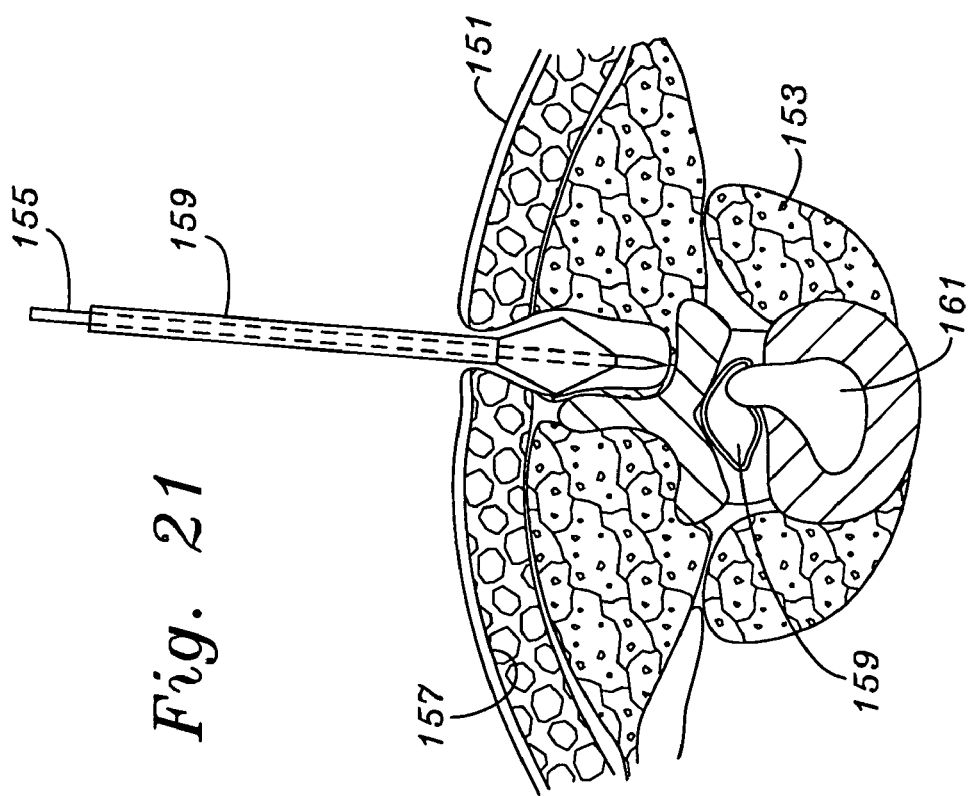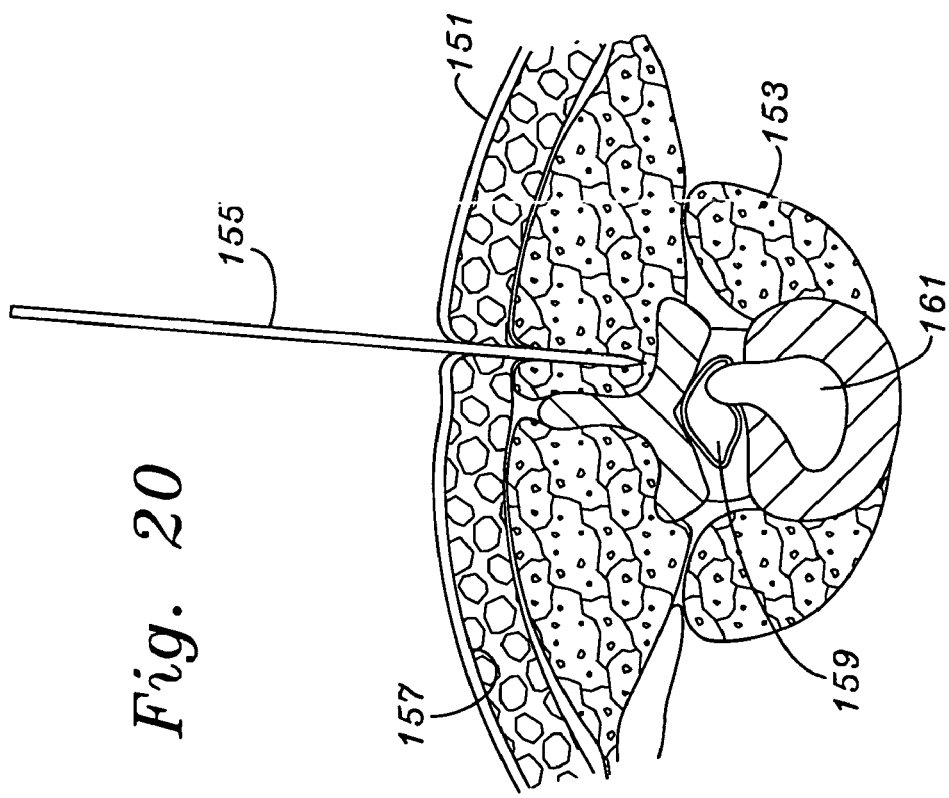

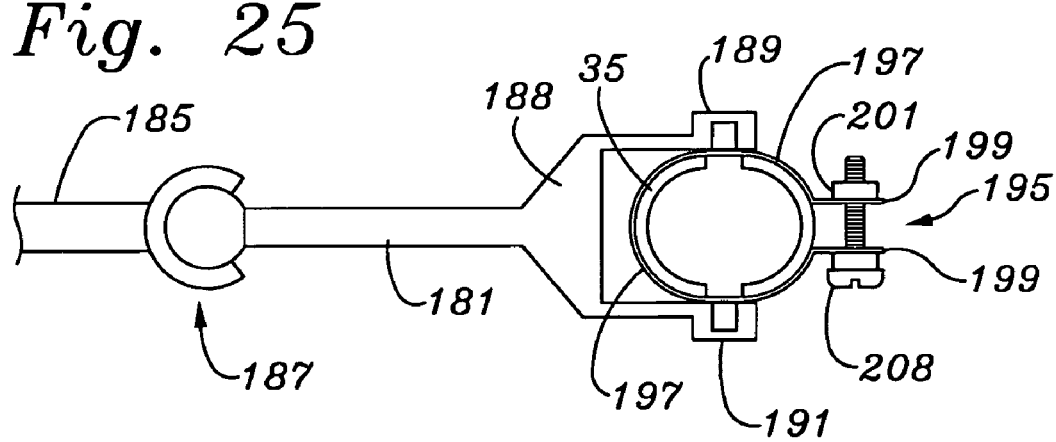
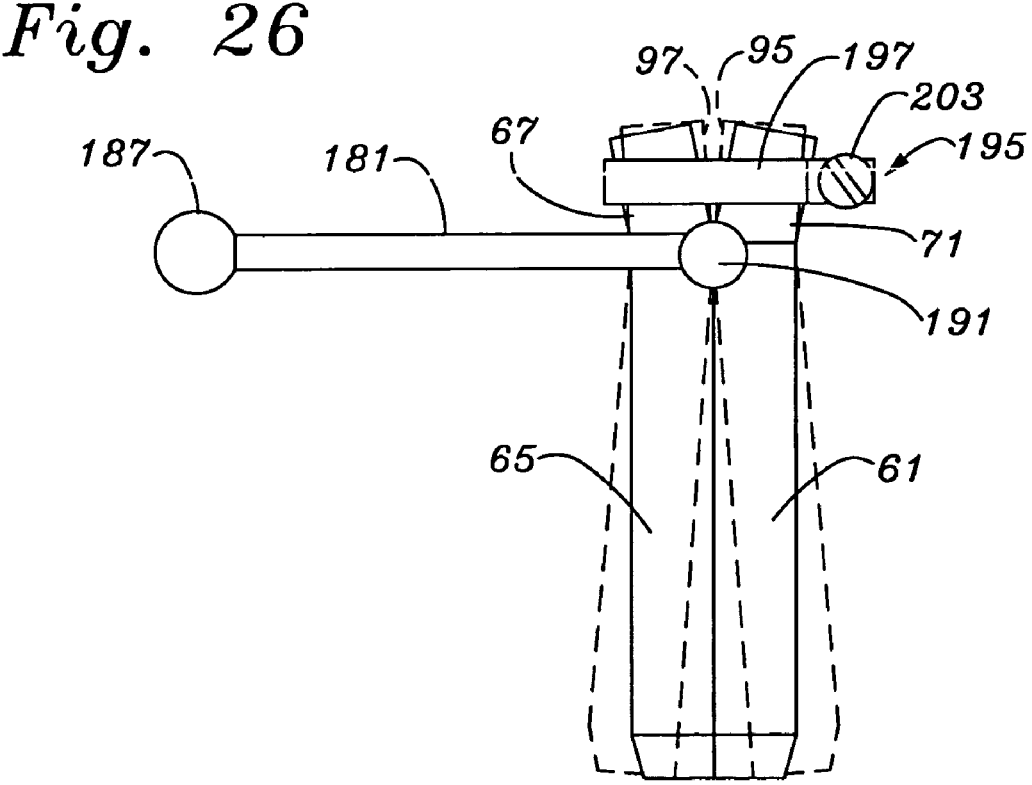

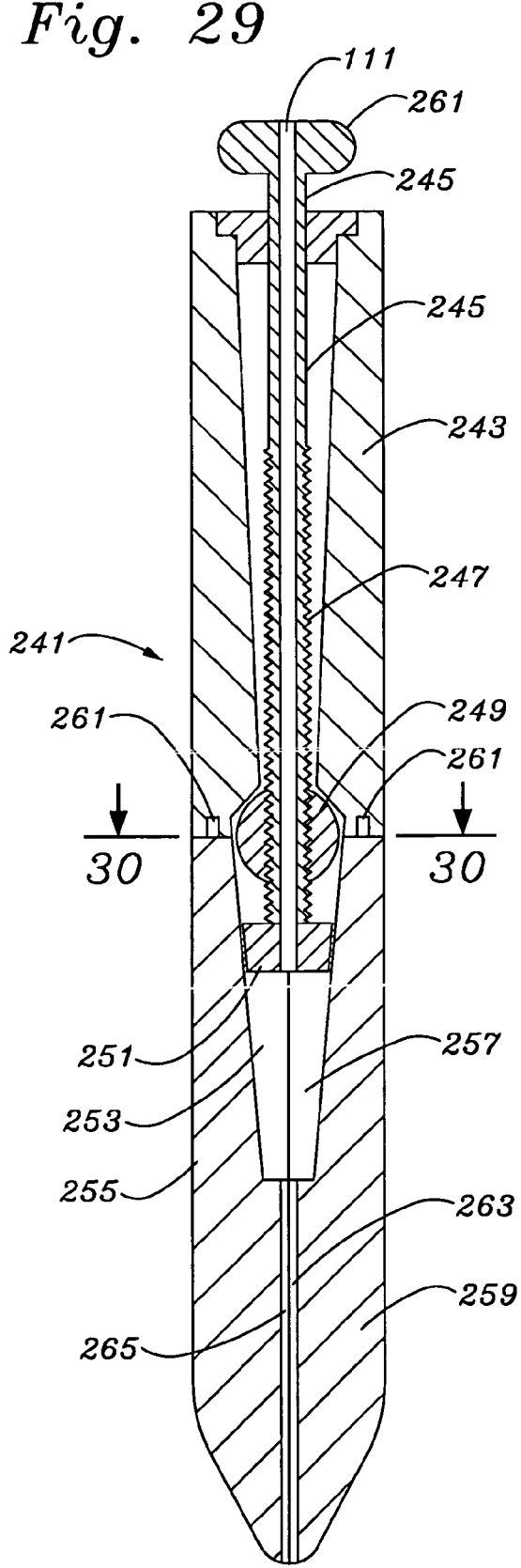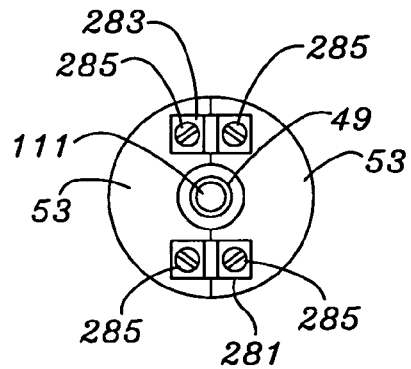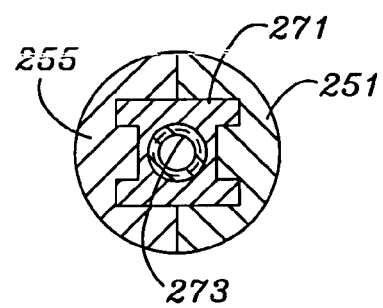

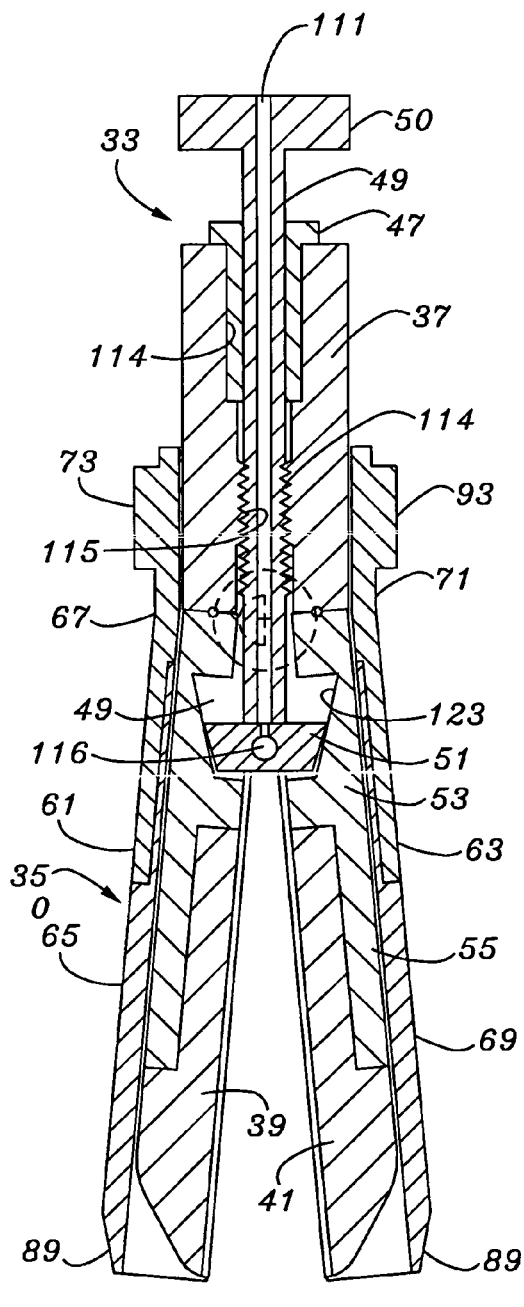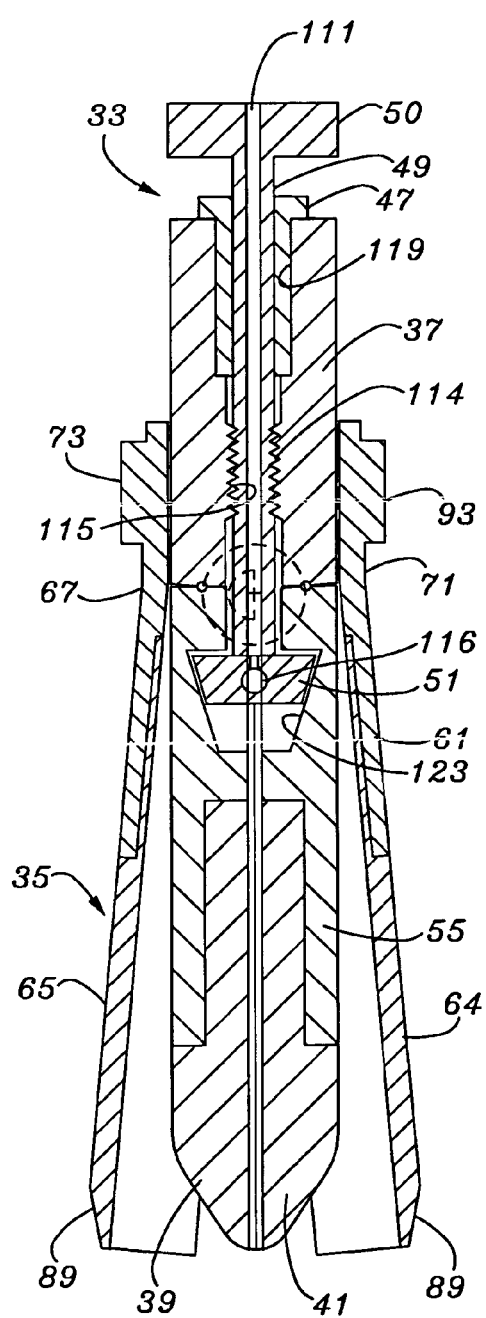

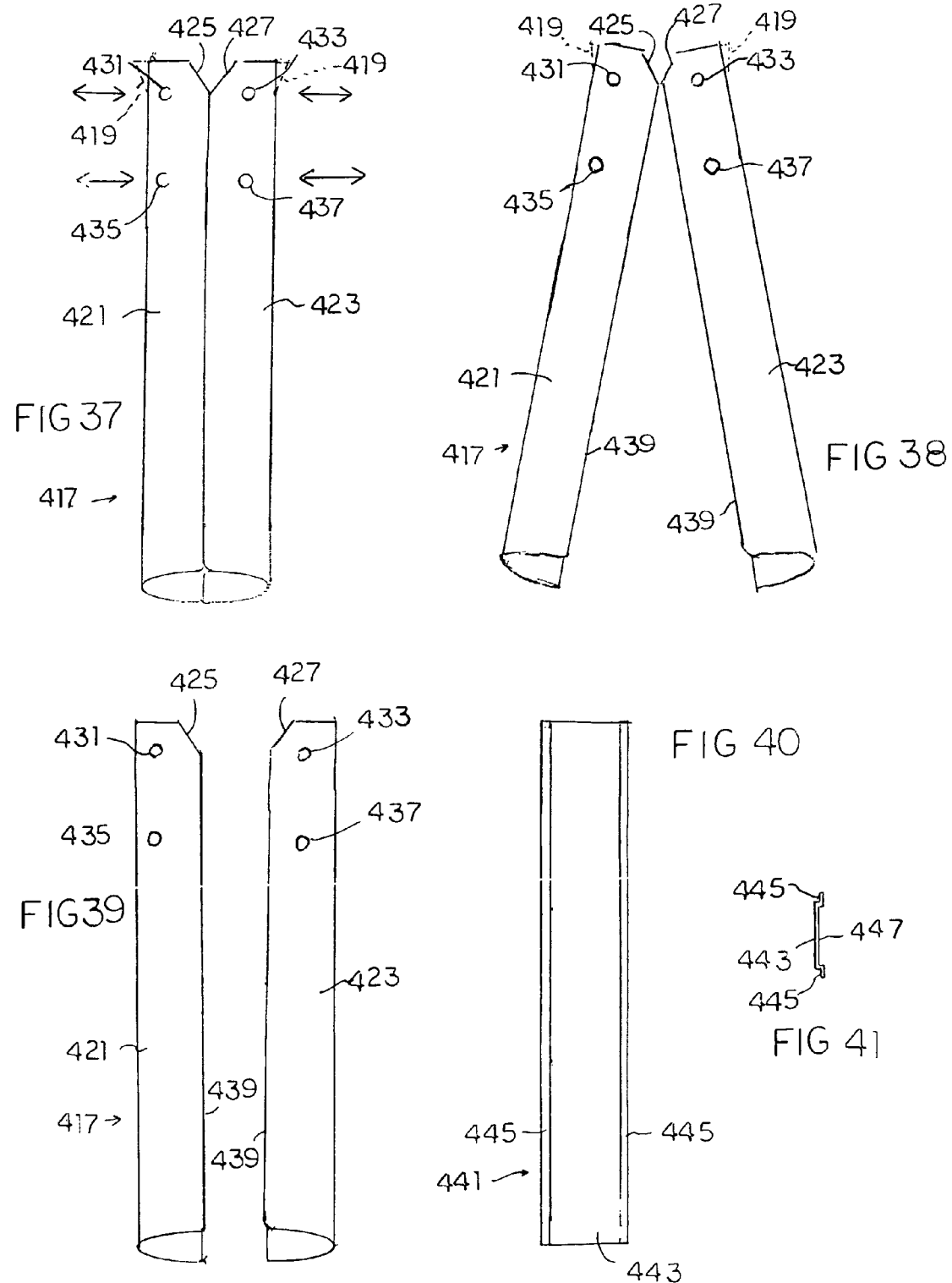

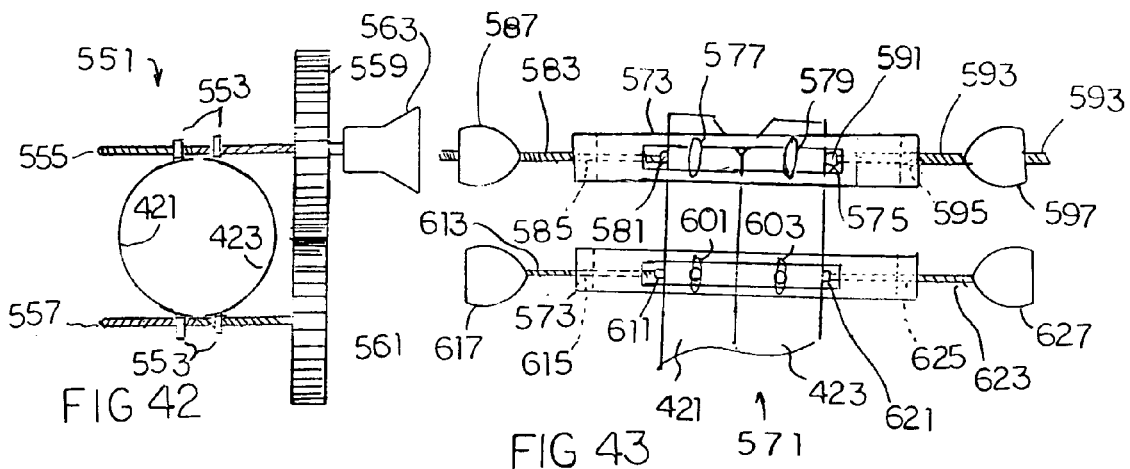
FIG 42
FIG 43
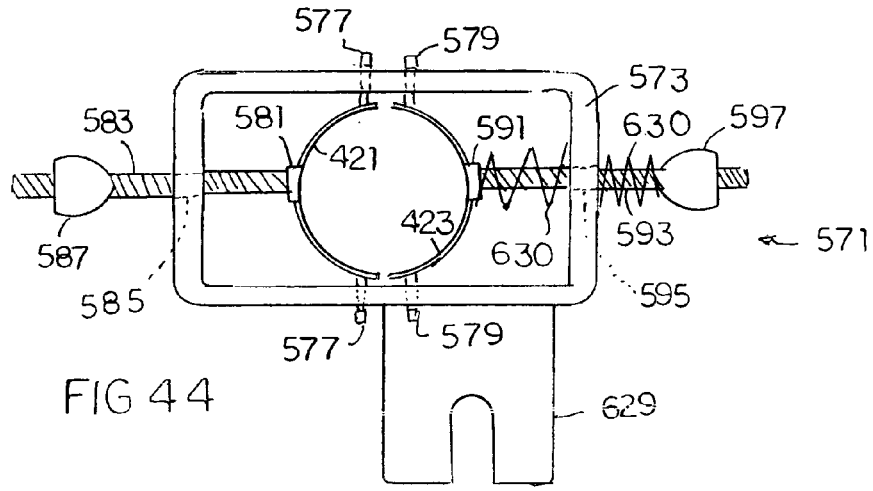
FIG 44
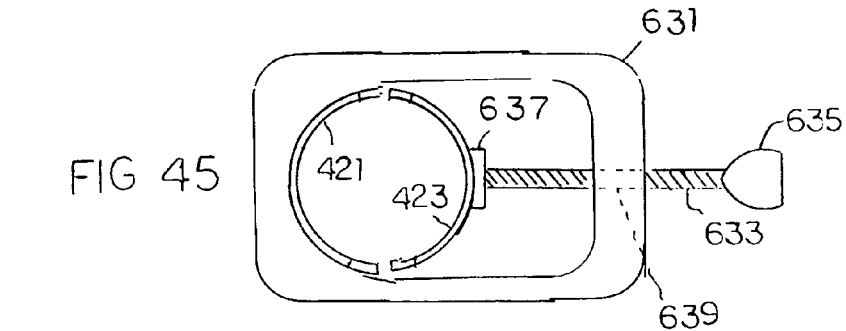
FIG 45

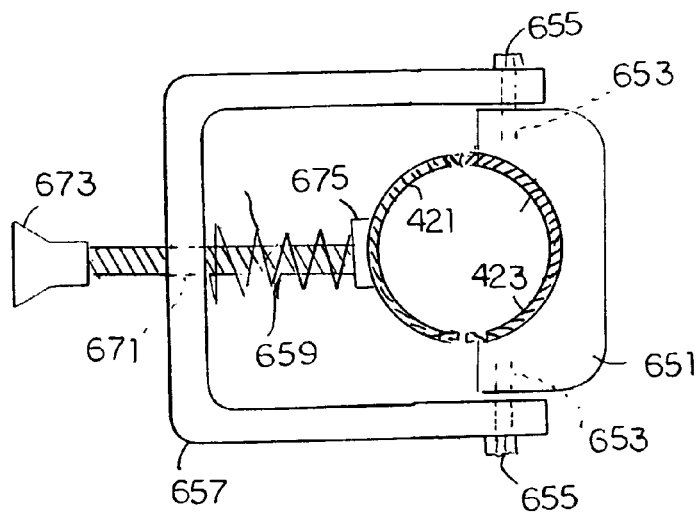
FIG 46
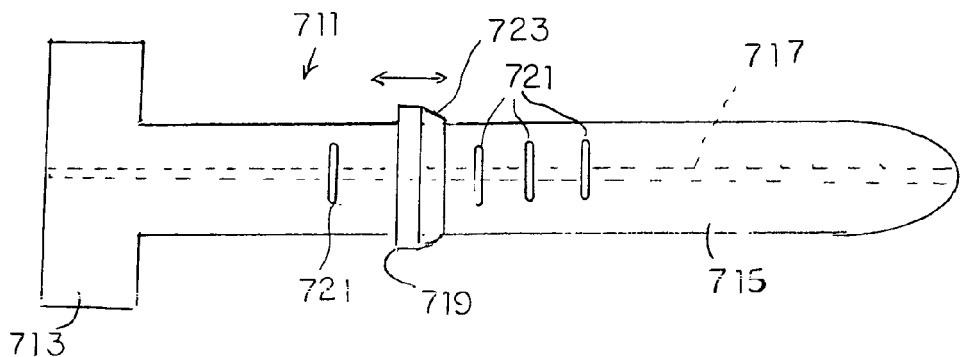
FIG 49
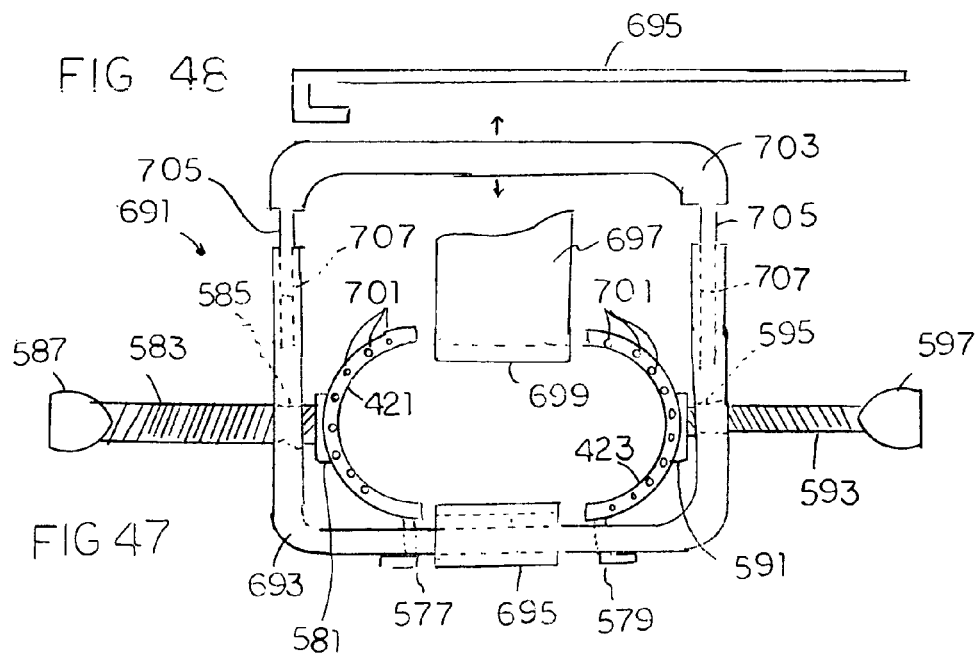
FIG 48
FIG 47

MINIMAL ACCESS LUMBAR DISKECTOMY INSTRUMENTATION AND METHOD

CROSS-REFERENCE TO RELATED APPLICATIONS

This application is a continuation-in-part application of U.S. patent application Ser. No. 11/001,628 filed Nov. 30, 2004 now U.S. Pat. No. 7,173,240, which is a divisional application of U.S. Ser. No. 10/280,624 filed Oct. 25, 2002, now U.S. Pat. No. 6,849,064, the entire contents of each of which are incorporated by reference herein.

FIELD OF THE INVENTION

The present invention relates to improvements in the field of minimal access lumbar posterior surgery and more particularly to instrumentation which allows for maximal access to the surgical field through the smallest possible incision. Greater access is allowed into the working field while enjoying the reduction of trauma and disturbance to surrounding tissues, which results in a reduced the time necessary to complete the operative procedure, increased safety of the procedure, and increased accuracy by providing an expanded working field.

BACKGROUND OF THE INVENTION

Microscopic Lumbar Diskectomy techniques were developed and championed by Dr. Robert Williams in the late 1970's and by Dr. John McCullough in the late 1980's and 1990's. For the first time since the advent of Lumbar Disc Surgery by Mixter and Barr in 1934 a method was introduced allowing Lumbar Disc Surgery to be performed through a small incision safely resulting in faster patient recovery and converting a two to five hospital stay procedure virtually to an outpatient procedure.

The special retractors developed by Drs. Williams and McCullough however were often difficult to maintain in optimum position and relied on the interspinous and supraspinatus ligaments for a counter fixation point severely stretching the structures. This stretching along with the effects of partial facectomy, diskectomy, removal of the ligamentum flavum and posterior longitudinal ligament contributed to the development of Post Diskectomy Instability. Taylor retractors were also used but were cumbersome, required larger incisions and often injured the facet joints.

Dr. William Foley in 1997 introduced a tubular system mated to an endoscope which he labeled a Minimal Endoscopic Diskectomy (MED) system. It featured sequentially dilating the Lumbar Paraspinous Muscles allowing a working channel to be advanced down to the level of operation through which nerve root decompression and Diskectomy Surgery could be performed with a small incision and less muscle trauma. Improvements were made by Dr. Foley in his second generation METRx system. However, there were several disadvantages to the MED and METRx systems.

In the MED and METRx systems, the cylindrical working channel considerably restricted visualization and passage of instruments. It also compromised the "angle of approach" necessary for safe usage of the operating instruments. This problem was proportionately aggravated with the long length of the tube. This compromised visualization contributed to the following problems, including nerve injury, dural tear, missed disc fragments, inadequate decompression of the lateral recess, increased epidural bleeding, difficulty controlling epidural bleeding, inadequate visualization of the neuroforamen, and inadequate decompression of neuroforamen.

The repetitive introduction of successively larger dilators caused skin abrasion with the potential for carrying superficial skin organisms down to the deeper tissue layers hypothetically increasing the risk of infection. The learning curve for operating in a two dimension endoscopic field proved to be arduous and contributed to the above complications.

The attempted use of the METRx for more complex procedures such as fusion was further hazardous by inherent limitations.

Endius in September of 2000 then introduced a similar device which differed by having an expandable foot piece to allow greater coverage of the operative field. However, the enlarged foot piece was unwieldy and difficult to seat properly. Exposure of the angle of approach was also limited by having to operate through a proximal cylindrical tube with its limitations as described before. In comparison to the METRx system the working area was improved but access was again restricted by the smaller proximal cylinder.

Both systems offered endoscopic capability but many spine surgeons chose to use an operating microscope or loupes to maintain 3-Dimensional visualization rather than the depth impaired 2-Dimensional endoscopic presentation. Keeping debris off of the endoscopic lens has also proved to be a troubling challenge.

SUMMARY OF THE INVENTION

The system and method of the invention, hereinafter minimal incision maximal access system, includes a surgical operating system that allows for maximum desirable exposure along with maximum access to the operative field utilizing a minimum incision as small as the METRx and Endius systems. The minimal incision maximal access system disclosed offers advantages over the METRx and Endius systems in several respects. First, instead of multiple insertions of Dilating Tubes the Invention is a streamlined single entry device. This avoids repetitive skin surface entry. Second, the minimal incision maximal access system offers the capability to expand to optimum exposure size for the surgery utilizing hinged bi-hemispherical or oval Working Tubes applied over an introducer Obturator which is controllably dilated to slowly separate muscle tissue.

Third, the minimal incision maximal access system maximizes deeper end working and visualization area with maximum proximal access and work dimensions significantly greater than either the METRx or Endius devices and methods. Fourth, the minimal incision maximal access system provides expanded visual and working field to makes the operative procedure safer in application and shorten the surgeons's learning curve because it most closely approximates the open microdiskectomy techniques. Fifthly, the minimal incision maximal access system has a tapered ended Obturator which allows for tissue spread rather than muscle tissue tear and subsequent necrosis.

Sixth, the minimal incision maximal access system controls muscle oozing into the operative field which is controlled by simply opening the tubes further. This also thereby controls the bleeding by pressure to the surrounding tissues. Seventh, in contrast to the cylindrical tube based systems such as the METRx and Endius the minimal incision maximal access system offers a larger working area in proportion to the working depth. For the first time this allows for a minimal access technique to be applied to the large or obese patients.

The enlarged footprint of the longer tubes in the minimal incision maximal access system is a major difference from any other minimal access system.

An eighth advantage of the minimal incision maximal access system is that ist expandable design allows for excellent exposure for more complex procedures such as fusion and instrumentation including TLIF, PLIF, and TFIF (Transfacet Interbody Fusion), as well as allowing application for anterolateral lumbar disc surgery. The minimal incision maximal access system can also be used for cervical surgery posteriorly (foraminotomy, lateral mass instrumented fusion) as well as anterior cervical diskectomy and fusion. The minimal incision maximal access system can also be used for anterior lumbar interbody fusion be it retroperitoneal, transperitoneal or laparoscopic.

A ninth advantage of the minimal incision maximal access system is that the medial oval cutout of the retractors, or sleeve forming the working tube, allows more central docking on the spine which is problematic for other devices. A medialized docking provides access for easier acid better and safer dural retraction to address midline pathology. A tenth advantage is had by including an anti-reflective inner surface of the retractor sleeves which eliminates unwanted glare.

An eleventh advantage of the minimal incision maximal access system includes the slanted and contoured distal end of the retractor sleeve which allows minimal resistance for entry and advancement to the docking site. A twelfth advantage minimal incision maximal access system is the provision of a variety of retractor tips specific for different surgical procedures.

A thirteenth advantage of the minimal incision maximal access system is the provision of oval retractor sleeves for larger access requirements such as pedicle to pedicle exposure and especially in the case where pedicle screw instrumentation is to be applied. This minimizes unnecessary muscle spread by providing a smaller waist profile than a circular system. A fourteenth advantage of the minimal incision maximal access system is that the larger retractor sleeve also features one or two "skirts" to cover the lateral aperture created by the spread of the two retractor sleeves when opened. This prevents soft tissue and muscle ingress into the working cone. The skirts are attached to the working tube either at the hinge or on one of the two halves of the sleeve.

A fifteenth advantage of the minimal incision maximal access system is the provision or a modular design in which the retractor sleeves can be quickly removed, changed and reapplied. In this version the proximal port can also be modular and changeable to fit the needs of a specific surgical procedure. A sixteenth advantage of the minimal incision maximal access system is that the retractor sleeves can be made out of metal, ceramic or plastic, can be opaque or translucent, and can have tips of different shapes for different applications. A seventeenth advantage is the provision of snap lock connections of the major parts of the Invention provides for easy assembly and disengagement for cleaning and sterilization purposes.

Further, the Obturator is cannulated for carrying a central Guide Pin Passage. It has a Handle component which remains superficial to the skin. The obturator houses an internal hinge device which allows for spread of the two obturator tips.

BRIEF DESCRIPTION OF THE DRAWINGS

The invention, its configuration, construction, and operation will be best further described in the following detailed description, taken in conjunction with the accompanying drawings in which:

FIG. 2 is a perspective assembled view illustrating the relative positions of the obturator and working tube;

FIG. 3 is a perspective assembled view illustrates the position of the obturator after it has been inserted into the working tube;

FIG. 6 is an side end view of the working tube of FIGS. 1-5 and illustrating predominantly one of the rigidly connected halves of the invention;

FIG. 7 is a side sectional view taken along line 7-7 of FIG. 6 and showing the internal bearing pivot;

FIG. 8 is a side sectional view taken along line 8-8 of FIG. 5 and illustrating a option for external bevel for the working tube;

FIG. 9 is a side view of the working tube of FIGS. 1-8 shown with the lower portions in parallel alignment and the upper portions angled with respect to each other;

FIG. 10 is a side view of the working tube as seem in FIG. 9 and shown with the lower portions in an angled relationship and the upper portions in a closer angled relationship with respect to each other;

FIG. 11 is a side view of the working tube as seen in FIGS. 9 and 10 and shown with the lower portions in a maximally angled relationship and the upper portions in parallel alignment signaling maximal spread of the lower portions in bringing the upper portions into parallel alignment;

FIG. 15 is a sectional view taken along line 14-14 of FIG. 12 and gives a sectional view from the same perspective seen in FIG. 14;

FIG. 16 is a view of the obturator similar to that seen in FIG. 15, but turned ninety degrees along its axis and illustrates the wedge as having a narrower dimension to lend internal stability;

FIG. 17 is a closeup view of the external hinge assembly seen in FIG. 1 and illustrates the optional use of a plug to cover the exposure side of a circular protrusion;

FIG. 18 is a view taken along line 18-18 of FIG. 11 and illustrates the use of an optional skirt having flexible members which spread from an initial curled position to a straightened position to better isolate the surgical field;

FIG. 20 is a cross sectional view of the a patient and spine and facilitates illustration of the general sequence of steps taken for many procedures utilizing the minimal incision maximal access system disclosed;

FIG. 21 illustrates a fascial incisor over fitting a guide pin and further inserted to cut through external and internal tissue;

FIG. 25 illustrates further details of the support arm seen in FIG. 24, especially the use of a ball joint;

FIG. 26 illustrates a side view of the assembly seen in FIG. 25 is seen with an adjustable clamp operable to hold the working tube open at any position;

FIG. 29 illustrates a further variation on the obturator seen previously in FIG. 1 and illustrates the use of a central ball nut;

FIG. 30 is a sectional view taken along line 30-30 of FIG. 29 and illustrates the use of a central support block to support the central threaded surface;

FIG. 31 is a top view of a thin, inset hinge utilizable with any of the obturators herein, but particularly obturators of FIGS. 1 and 29;

FIG. 32 is a sectional view of the obturator of FIG. 1 within the working tube of FIG. 1 with the wedge 51 seen at the bottom of an internal wedge conforming space;

FIG. 33 illustrates the obturator seen in FIG. 32 as returned to its collapsed state.

FIG. 37 is an isolated view of two hemicylindrical tube sections shown joined in a tubular relationship and indicating at least a pair of pivot axes on each hemicylindrical tube section;

FIG. 38 is an isolated view of two hemicylindrical tube sections as seen in FIG. 38 which are angularly displaced apart about a shared first pivot axis on each of the hemicylindrical tube sections;

FIG. 39 is an isolated view of two hemicylindrical tube sections as seen in FIGS. 38 and 39 which are angularly displaced apart about a shared second pivot axis on each of the hemicylindrical tube sections;

FIG. 40 is a plan view of a given width supplemental side shield having a width of approximately the separation of the hemicylindrical tube sections as seen in FIG. 39;

FIG. 41 is a top view of the supplemental side shield of FIG. 40;

FIG. 42 is a pivoting thread support system in which a pair of opposing flank threaded members operate a pivoting support and are connected by a gear mechanism shown in exaggerated format to give single knob separation control;

FIG. 43 illustrates a surrounding frame system utilized to provide and enable pivoting and translation;

FIG. 44 illustrates a view looking down into the structure of FIG. 43 shows the overall orientation and further illustrates an optional securing tang;

FIG. 45 illustrates a simplified control scheme in which simplicity is emphasized over controllability with less moving parts and expense;

FIG. 46 illustrates a further embodiment of a manipulative structure which works well with the structure of FIG. 45; and FIG. 47 illustrates another possible realization which combines the control mechanisms of selected portions of FIGS. 37-46, combined with other possible options.

FIG. 48 illustrates another side view of the side shield; and

FIG. 49 illustrates a variable depth guide which combines with any of the devices of FIGS. 37-46.

DETAILED DESCRIPTION OF THE PREFERRED EMBODIMENT

Figure 1:
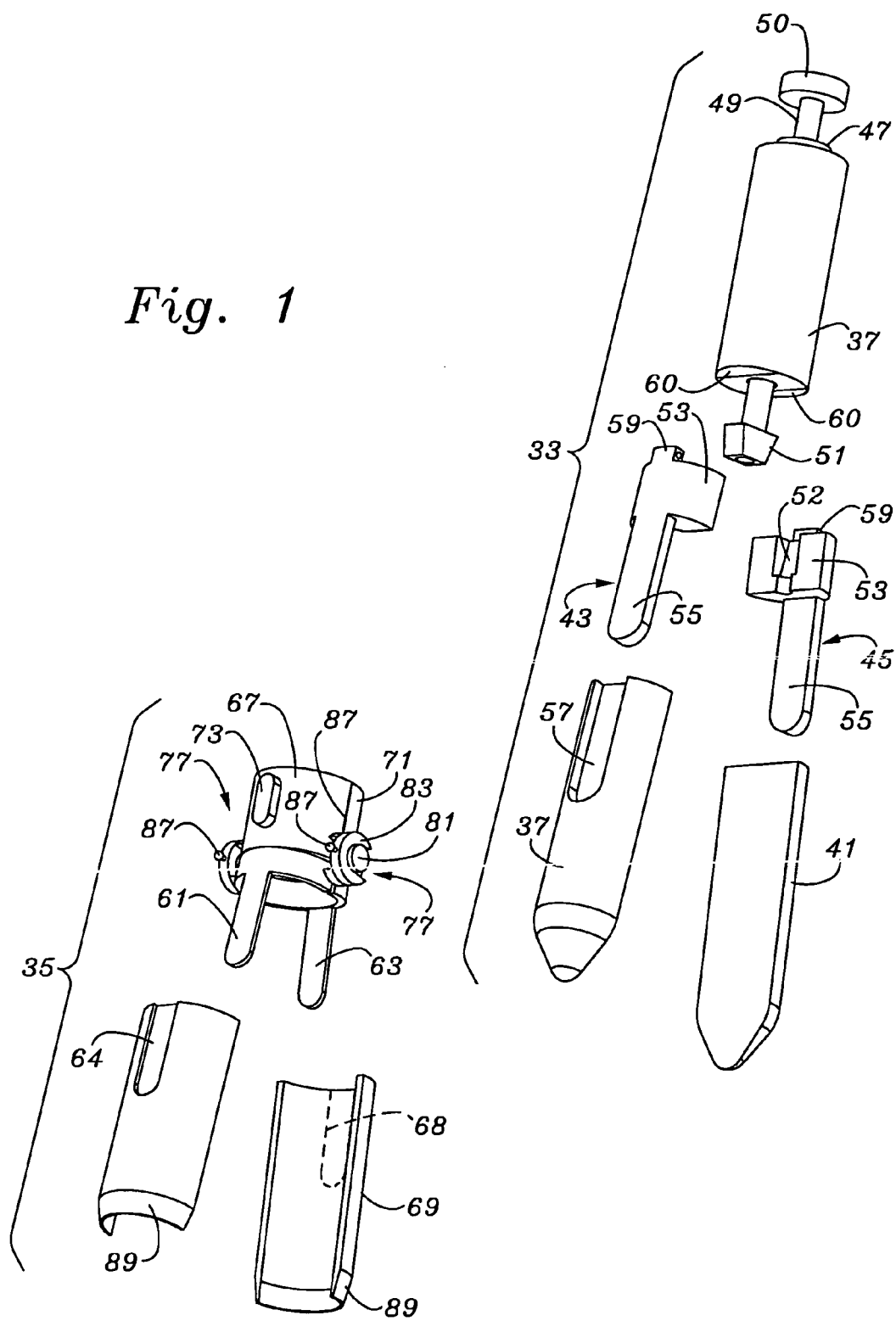
FIG. 1 is a perspective view of a working tube with an angled upper section and shown in position with respect to an obturator insertable into and workable within the working tube.

The description and operation of the minimal incision maximal access system will be best described with reference to FIG. 1 and identifying a general system 31. System 31 includes an obturator 33 and a working tube 35. The orientation of the obturator 33 is in a slightly displaced from a position of alignment with the working tube 35 for entry into working tube 35 and to provide the initial carefully controlled force for spreading the working tube 35, as will be shown.

Obturator includes an upper control housing 37 and a pair of spreading legs 39 and 41. The spreading legs 39 and 41 are seen as coming together to form a conical tip and thus have hemi-conical end portions. The spreading legs 39 and 41 over fit the attachment leg portions 43 and 45, respectively. At the top of the upper control housing 37 a boss 47 surrounds and supports the extension of a control shaft 49. a knurled thumb knob 50 sits atop the control shaft 49 to facilitate controlled turning of the control shaft 49 to control the degree of spreading of the spreading legs 39 and 41. Thus spreading can be controlled independently of pressure applied along the length of the obturator 33.

Below the upper control housing 37 is the bottom of the control shaft 49 which operates against a wedge 51. The wedge 51 operates within a pair of opposing slots 52 in an upper portion 53 of the overfit attachment leg portions 43 and 45. The lower ends of the overfit attachment leg portions 43 and 45 include insertion tangs 55 which fit within insertion slots 57 of the spreading legs 39 and 41. The overfit attachment leg portions 43 and 45 are pivotally attached to the upper control housing 37 internally by pivot blocks 59 which fit within access apertures 60.

The working tube 35 has a first lower extending connection tang 61 and a second lower extending connection tang 63. First lower extending connection tang 61 connects into a slot 64 of a lower tube hemicylindrical portion 65. The first lower extending connection tang 61 is fixed to an upper angled hemicylindrical portion 67. The second lower extending connection tang 63 connects into a slot 68 of a lower tube hemicylindrical portion 69. Second lower extending connection tang 61 is fixed to and an upper angled hemicylindrical portion 71. The upper angled hemicylindrical portion 67 has a reinforced wear plate 73 for applying upper pressure and force on the upper angled hemicylindrical portions 67 and 71 toward each other to cause the first and second lower extending connection tangs 61 & 63 and their connected lower tube hemicylindrical portions 65 and 69 to be urged away from each other.

At the side of the working tube 35 at the transition between the upper angled hemicylindrical portions 67 and 71 and a point just above the first and second lower extending connection tangs 61 & 63 is an external hinge assembly 77. Hinge assembly 77 may include an optional first guide plate 79 and first circular protrusion 81 attached to upper angled hemicylindrical portions 67, and a first slotted plate 83 positioned adjacent to first guide plate 79 and having a slot partially surrounding the circular protrusion 81.

Upper angled hemicylindrical portion 71 has a pair of spaced apart facing surfaces facing a matching pair of facing surfaces of the upper angled hemicylindrical portion 67, of which a dividing line 85 is seen. Upper angled hemicylindrical portions 67 and 71 are be brought together to cause the first and second lower extending connection tangs 61 & 63 and their connected lower tube hemicylindrical portions 65 and 69 to spread apart.

In the View of FIG. 1, the first and second lower extending connection tangs 61 & 63 are shown in a spread apart relationship. a locking pin 87 is seen which can be used to engage angularly spaced apart apertures in the circular protrusion 81 to provide a detent action to hold the working tube 35 in various degrees of spread. Also seen is a slight exterior bevel 89 on the lower tube hemicylindrical portions 65 and 69.

Note the angled separation of the upper angled hemicylindrical portions 67 and 71 and exposing opposing surfaces 91. The angle of the opposing surfaces 91 equals the angle of spread of the first and second lower extending connection tangs 61 & 63.

Referring to FIG. 2, a perspective assembled view illustrates the relative positions of the obturator 33 and working tube 35 in a position for the obturator 33 to be inserted into the working tube 35 and before any spreading takes place.

Referring to FIG. 3, a perspective assembled view illustrates the position of the obturator 33 after it has been inserted into the working tube 35 and again before any spreading takes place. Note that the pivot axes of the first and second lower extending connection tangs 61 & 63 are on par with the pivot axes of the insertion tangs 55. The tip of the obturator 33 extends slightly beyond the beyond the bottom most part of the working tube 35 so that the completed assembly can be smoothly urged past muscle and other tissue.

Figure 4:
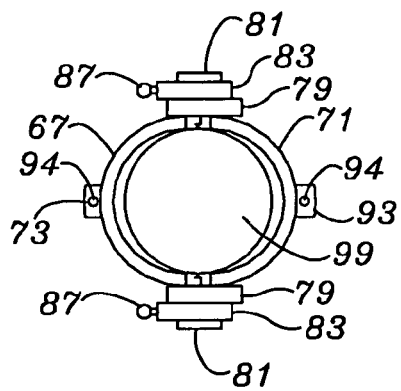
FIG. 4 is a view taken along line 4-4 of FIG. 2 and looking into the working tube of FIG. 1.

Referring to FIG. 4, a view taken along line 4-4 of FIG. 1 is a view looking down into the working tube 35. Other features seen include a wear plate 93 located on the upper angled hemicylindrical portion 71. In both of the wear plates 73 and 93 a universal port 94 is provided as a bore for insertion of a tool or lever to assist in bringing the upper angled hemicylindrical portions 67 and 71 into a tubular relationship. Further, an identical hinge assembly 77 on the side opposite that seen in FIG. 1 is shown with the same numbering as the components which were seen in FIG. 1.

Also seen are a pair of opposing surfaces 95 on upper angled hemicylindrical portion 71 and a pair of opposing surfaces 97 on upper angled hemicylindrical portion 67. Also seen is a central working aperture 99.

Figure 5:
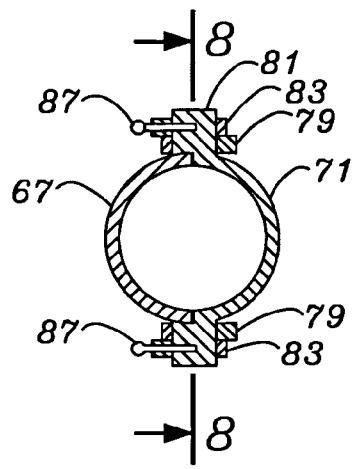
FIG. 5 is a sectional view taken along line 5-5 of FIG. 2 and looking into the hinge of working tube of FIG. 1, illustrating its hinge connections.

Referring to FIG. 5, a view taken along line 5-5 of FIG. 1 is a sectional view looking down into the working tube 35. The connectivity of the structures seen in FIG. 4 are emphasized including the connection of circular protrusion 81 to the upper angled hemicylindrical portion 71, and the connection of first slotted plate 83 to upper angled hemicylindrical portion 67, and which is indicated by the matching section lines Further, an identical hinge assembly 77 on the side opposite that seen in FIG. 1 is shown with the same numbering as the components which were seen in FIG. 1.

Referring to FIG. 6, a view of one end of the working tube 35 illustrates predominantly the second angled half portion 63. Elements seen in FIGS. 1 and 2 are made more clear in FIG. 3.

Referring to FIG. 7, a side sectional view taken along line 7-7 of FIG. 6 and shows the internal bearing pivot consisting of a slightly greater than hemispherical side bump projection 101 located on upper angled hemicylindrical portion 71, and a slightly less than hemispherical side circular groove 103 located on upper angled hemicylindrical portion 67. Also seen is the interconnect slots 64 and 68 as well as the first and second lower extending connection tangs 61 and 63. In the showing of FIG. 7 an external bevel 105 is utilized Referring to FIG. 8, a side semi-sectional view taken along line 8-8 of FIG. 5 illustrates the integral connectivity of circular protrusion 81 with the upper angled hemicylindrical portion 71. Seen for the first time in isolation are a pair of pin apertures 107 for engaging the locking pin 87.

Referring to FIG. 9, an illustration of a side plan view and in which the lower tube hemicylindrical portions 65 and 69 are in matching straight alignment and forming a lower tube shape, while the upper angled hemicylindrical portions 67 and 71 are angled apart.

Referring to FIG. 10, a midpoint of movement is illustrates wherein the lower tube hemicylindrical portions 65 and 69 have begun to move apart widening the lower tube shape previously formed into an angled apart opposing hemicylindrical shape, while the upper angled hemicylindrical portions 67 and 71 are brought closer together to have a closer though angled apart an angled apart opposing hemicylindrical shape.

Referring to FIG. 11, a completed movement, with respect to the view of FIG. 4 illustrates a state where the lower tube hemicylindrical portions 65 and 69 have moved apart to their maximum extent into a maximally angled apart opposing hemicylindrical shape, while the upper angled hemicylindrical portions 67 and 71 are brought completely together to form an upper tube shape. It is the position of FIG. 6 which is the ideal working position once the lower tube hemicylindrical portions 65 and 69 are within the body, and provides an expanded working field at the base of the working tube 35. Surgical work is ideally performed through the upper, abbreviated axial length tube shape formed by the upper angled hemicylindrical portions 67 and 71.

Figure 12:
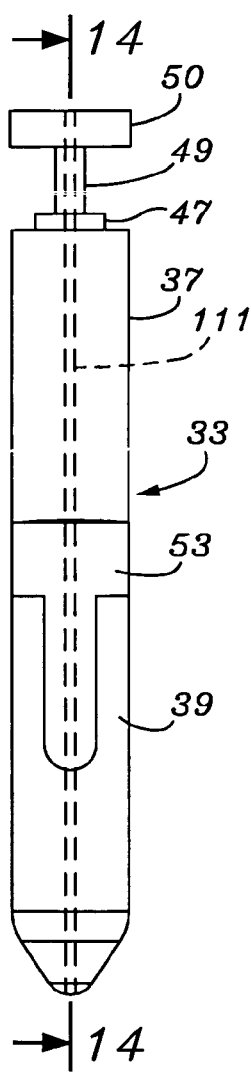
FIG. 12 is a side view of the obturator of FIG. 1 and seen in an assembled view and emphasizing a through bore seen in dashed line format.

Referring to FIG. 12, a side view of the obturator 33 of FIG. 1 is seen in an assembled view and emphasizing in dashed line format a through bore 111 which extends though the obturator 33 from the knurled knob 50 through to the tip of the pair of spreading legs 39 and 41.

Figure 13:
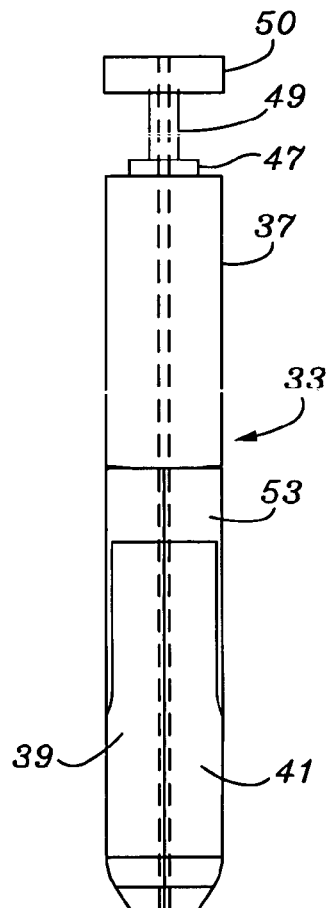
FIG. 13 is a side view of the obturator of FIG. 11 as seen in an assembled view but turned ninety degrees about its axis and emphasizing the through bore.

Referring to FIG. 13, a side view of the obturator 33 of FIG. 11 is seen in an assembled view but turned ninety degrees about its axis, and aging emphasizing in dashed line format the through bore 111 which extends though the obturator 33 from the knurled knob 50 through to the tip of the pair of spreading legs 39 and 41. It is from this position that further actuation will be illustrated.

Figure 14:
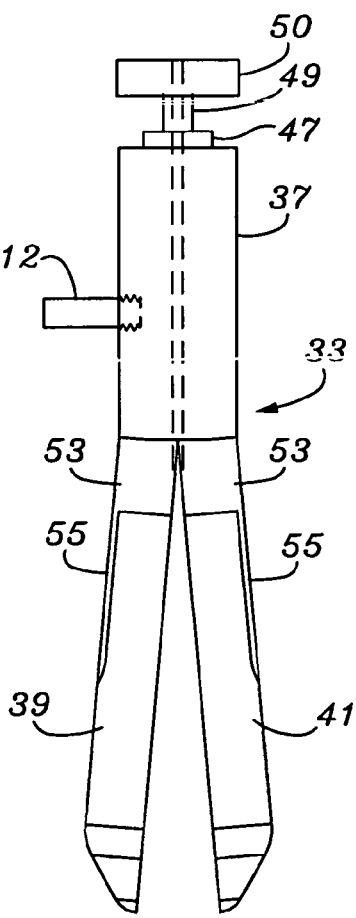
FIG. 14 shows a side view of the obturator 33 of FIG. 13 with the spreading legs in an angled apart relationship.

Referring to FIG. 14, a side view of the obturator 33 of FIG. 13 is seen but with the spreading legs 39 and 41 in an angled apart relationship. An optional support 112 is supported by the upper control housing 37 to enable independent support and location of the obturator 33 should it be needed. Once the knurled knob 50 is turned, the wedge 51 seen in FIG. 1 is driven downward causing the spreading of the spreading legs 39 and 41.

Referring to FIG. 15, a sectional view taken along line 14-14 of FIG. 12 gives a sectional view from the same perspective seen in FIG. 14. Pivot blocks 59 are seen as having pivot bores 113 which enable the upper portions 53 to pivot with respect to the upper control housing 37 and which enable the downward movement of the wedge 51 to translate into a spreading of the spreading legs 39 and 41.

As can be seen, the knob 50 and control shaft 49 and the wedge 51 have the through bore 111. In the configuration shown, the control shaft 49 includes a threaded portion 113 which engaged an internally threaded portion 115 of an internal bore 117 of the upper control housing 37. The boss 47 is shown to be part of a larger insert fitting within a larger fitted bore 119 within the upper control housing 37. This configuration pushes the wedge 51 downwardly against an internal wedge conforming space 123 to cause the insertion tangs 55 and upper portions 53 to spread apart. The wedge conforming space 123 need not be completely wedge shaped itself, but should ideally have a surface which continuously and evenly in terms of area engages the wedge 51 to give even control. Further, the wedge 51 can be configured to be rotatable with or independently rotationally stable with respect to the control shaft 49. As can be seen, the through bore 111 continues below the internal wedge conforming space 123 as a pair of hemicylindrical surfaces 125 in the upper portion 53, as well as a pair of hemicylindrical surfaces 127 in the pair of spreading legs 39 and 41.

Referring to FIG. 16 a view of obturator 33 similar to that of FIG. 15, but turned ninety degrees along its axis is seen. In this view, the wedge 51 is seen as having a narrower dimension to lend internal stability by narrowing the bearing area of the wedge 51 action in opening the pair of spreading legs 39 and 41.

Referring to FIG. 17, a closeup view of the external hinge assembly 77 seen in FIG. 1 illustrates the optional use of a plug 131 to cover the exposed side of the circular protrusion 81.

Referring to FIG. 18, a view taken along line 18-18 of FIG. 11 illustrates a view which facilitates the showing of an optional skirt, including a skirt section 133 welded or otherwise attached to lower tube hemicylindrical portion 65, and a skirt section 133 welded or otherwise attached to lower tube hemicylindrical portion 69. The skirts sections 133 and 135 are made of thin flexible metal and interfit within a pair of accommodation slots 137 and 139, respectively.

Figure 19:
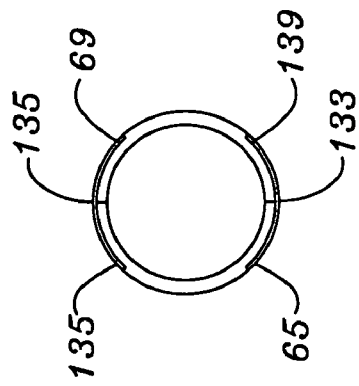
FIG. 19 is a view of the lower tube hemicylindrical portions 65 and 69 in a close relationship illustrating the manner in which the skirts sections within their accommodation slots areas.

Referring to FIG. 19, a view of the lower tube hemicylindrical portions 65 and 69 in a close relationship illustrates the manner in which the skirts sections 133 and 135 fit within the accommodation slots 137 and 139 when the lower tube hemicylindrical portions 65 and 69 are brought together to a circular configuration.

Referring to FIG. 20, a cross sectional view of the a patient 151 spine 153 is shown for illustration of the general sequence of steps taken for any procedure utilizing the minimal incision maximal access system 31. There are several procedures utilizable with the minimal incision maximal access system 31. Only a first procedure will be discussed using illustrative figures. Other procedures will be discussed after minor variations on the minimal incision maximal access system 31 are given below.

Procedure I: Diskectomy and Nerve Decompression

The patient 151 is placed prone on radiolucent operating table such as a Jackson Table. The patient 151 is then prepared and draped. The operative area is prepared and localized and an imaging device is prepared. A guide pin 155 is insert through the patient's skin 157, preferably under fluoroscopic guidance. In the alternative and or in combination, the patient 151 skin can be incised with a scalpel. Other features in FIG. 20 include the dural sac 159, and ruptured intervertebral disc 161.

Referring to FIG. 21, a fascial incisor 169 overfits the guide pin 155 and is further inserted to cut through external and internal tissue. The fascial incisor 169 is then removed while the guide pin 155 is left in place. Next, using the obturator 33, the surgeon clears the multifidus attachment with wig-wag motion of the obturator 33 tip end. Next the obturator 33 is actuated to gently spread the multifidus muscle, and then closed.

Figure 22:
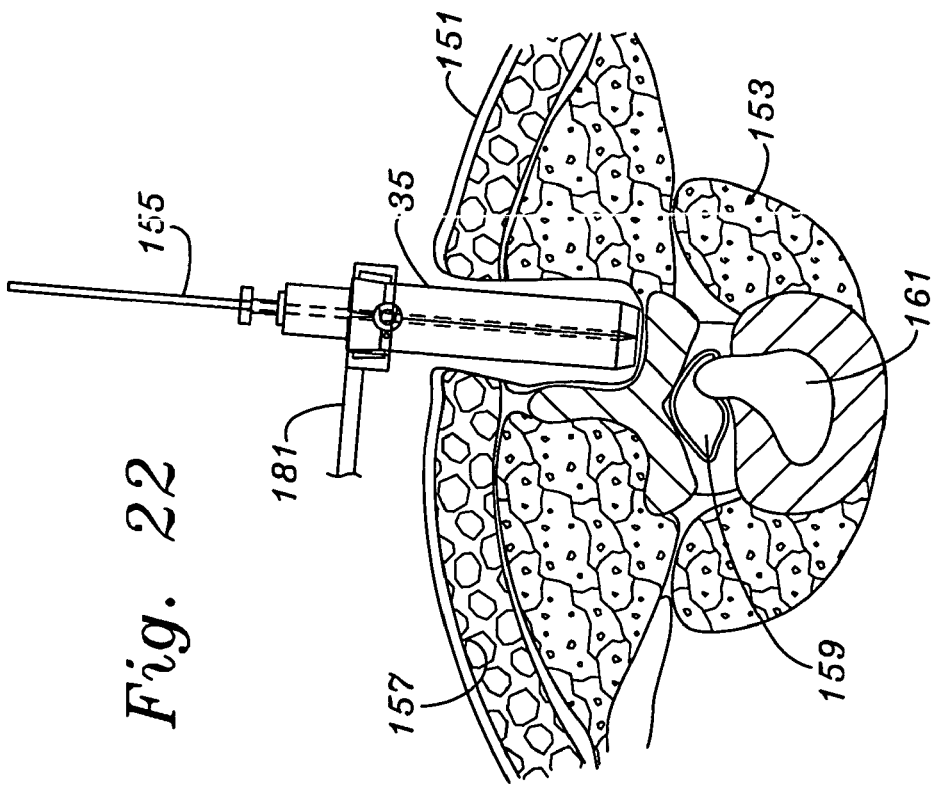
FIG. 22 illustrates the assembled Working Tube-Obturator being inserted into the area previously occupied by the fascial incisor and advanced to the operative level lamina.

Referring to FIG. 22, next the assembled Working Tube 35-Obturator 33 is inserted into the area previously occupied by the fascial incisor 169 and advanced to the operative level lamina and remove the obturator 33. As an alternative, and upon having difficulty, the obturator 33 could be initially inserted, followed by an overfit of the working tube 35. In another possibility, a smaller size of obturator 33 and working tube 35 or combination thereof could be initially utilized, followed by larger sizes of the same obturator 33 and working tube 35. The assembled Working Tube 35-Obturator 33 in place is shown in FIG. 22 with the working ends very near the spine.

Figure 23:
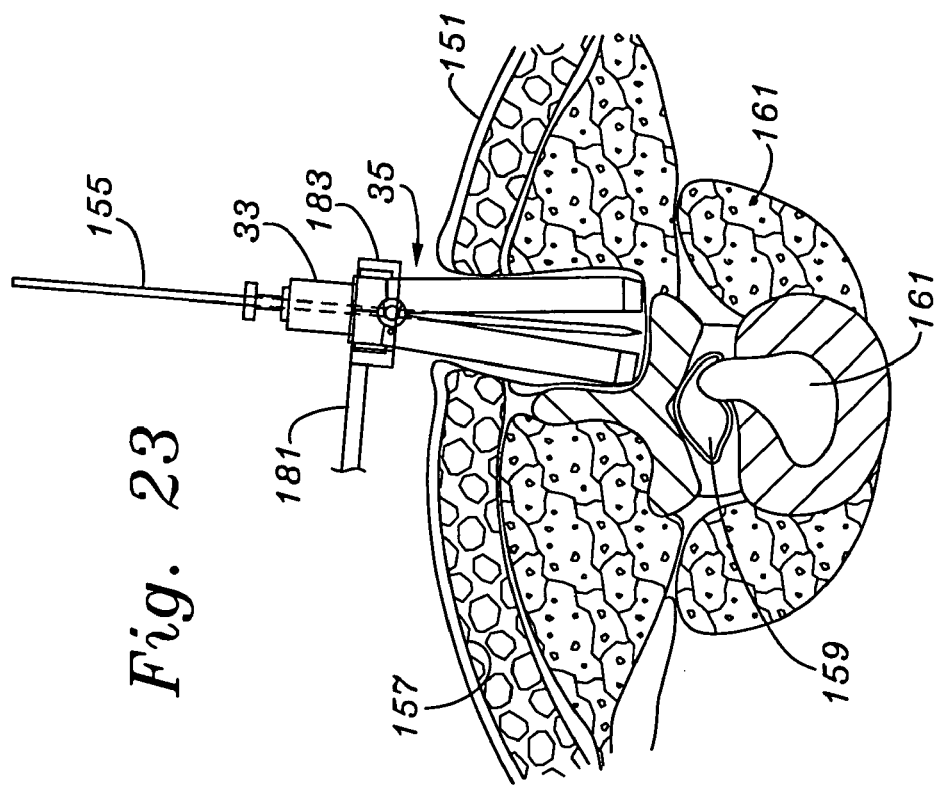
FIG. 23 illustrates the obturator 33 being actuated to a spread orientation to which automatically actuates the working tube to a spread orientation.

Referring to FIG. 23, the obturator 33 is actuated to a spread orientation, which automatically actuates the working tube 35 to a spread orientation. Spread is had to the desired exposure size. The obturator 33 is thin actuated to a closed or non-spreading position. The obturator and working tube is then again advanced to dock on the spine. The working tube 35 is then fixed to assume an open position either by utilization of the locking pin 87 or other fixation device to cause the working tube 35 to remain open. Then, once the working tube 35 is locked into an open position, the obturator 33 is actuated to a closed or non-spread position and gently removed from the working tube 35.

Figure 24:
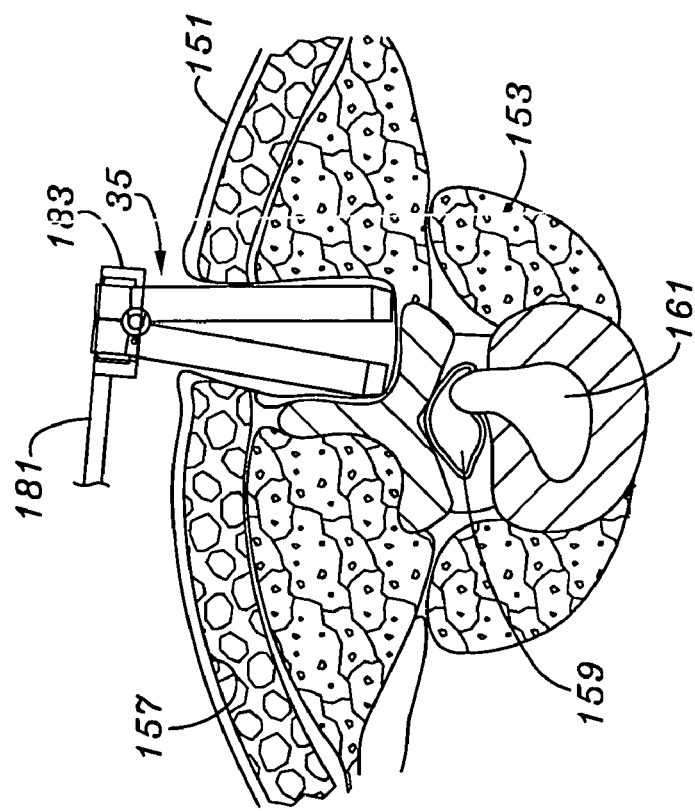
FIG. 24 is a view of the working tube 35 is in place and supported, held or stabilized in the field of view by a telescopy support arm and engagement, the opposite end of the stabilizing structure attached to the operating table.

Referring to FIG. 24, the working tube 35 is in place. The working tube 35 may be secured by structure ultimately attached to an operating table. The working tube 35 may be held or stabilized in the field of view by a support 181 which may have an engagement sleeve 183 which fits onto the working tube. As can be seen, the operative field adjacent the spine area is expended even though the incision area is limited. The deeper a given size of working tube 35 is inserted, the smaller its entrance area. After the working tube 35 is stabilized, the surgeon will typically clear the remaining multifidus remnant at the working level and then set up and insert an endoscope or use operating microscope or loupes. The surgeon is now ready to proceed with laminotomy.

Referring to FIG. 25, further detail on the support 181 and engagement sleeve 183 is shown. A base support 185 may support a ball joint 187, which may in turn support the support 181. The support 181 is shown as supporting a variation on the engagement sleeve 183 as a pivot point support engagement end 188 having arm supports 189 and 191. The arm supports 189 and 191 engage the external pivot structure on the working tube 35 which was shown, for example, in FIG. 1 to be the external hinge assembly 77.

As a further possibility, the upper angled hemicylindrical portions 67 and 71 are shown as being engaged about their outer periphery by an adjustable clamp 195. Adjustable clamp 195 includes a band 197 encircling the upper angled hemicylindrical portions 67 and 71. The ends of band 197 form a pair of opposing plates 199 and are engaged by a nut 201 and bolt 203 assembly.

Figure 27:
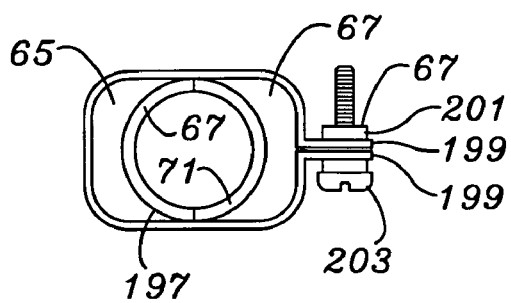
FIG. 27 is a top view looking down upon the adjustable clamp seen in FIGS. 25-26 and shows the orientation of the working tube and adjustable clamp in fully closed position.

Referring to FIG. 26, a side view of the assembly seen in FIG. 25 is seen with the adjustable clap 195 operable to hold the working tube 35 open at any position. Referring to FIG. 27, a top view looking down upon the adjustable clamp 195 seen in FIGS. 25-27 shows the orientation of the working tube 35 and adjustable clamp 195 in fully closed position. When used in conjunction with the adjustable clamp 195, the Reinforced wear plates 73 and 93 are eliminated so as to provide a smooth interface against the exterior of the upper angled hemicylindrical portions 67 and 71.

Figure 28:
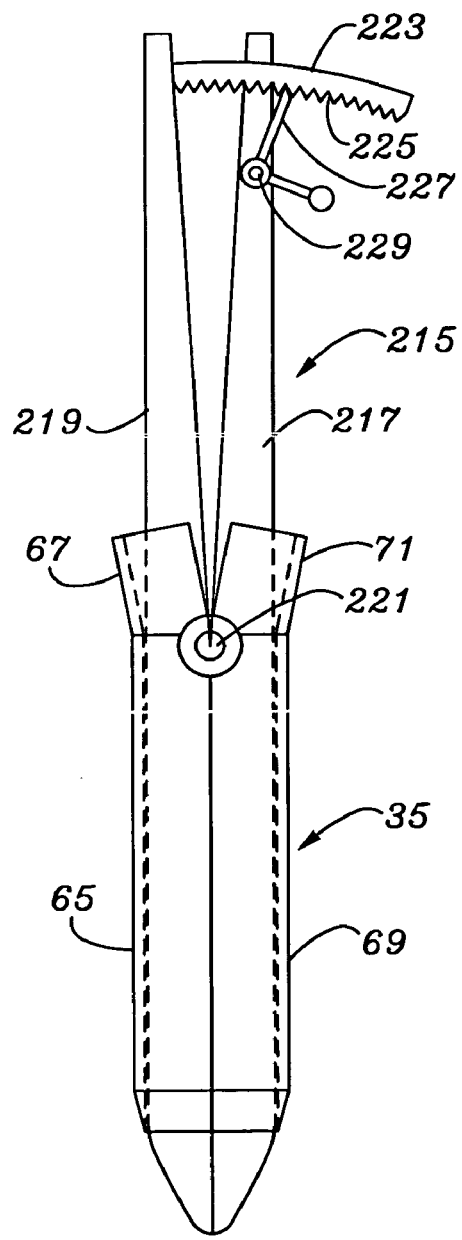
FIG. 28 shows a variation on the obturator seen previously in FIG. 1 and illustrates the use of handles which are brought together.

Referring to FIG. 28, a variation on the obturator 33 is seen. An obturator 215 has handles 217 and 219 which operate about a pivot point 221. A working tube 222 is somewhat simplified but is equivalent to the working tube 35 and is shown as including upper angled hemicylindrical portions 67 and 71. Handle 219 has a ratchet member 223 extending from it and a latch 227 pivotally connected about pivot point 229 to handle 217.

Referring to FIG. 29, a variation on obturator 33 is seen as an obturator 241 having an upper housing 243, control shaft 245 having a threaded section 247 and operating through a ball nut 249. A wedge 251 is extendable down through an operation space made up of a half space 253 in a leg 255 and a half space 257 in a leg 259. Hinge structures 261 are shown attaching the legs 255 and 259 to the upper housing 243. A through bore 111 is also seen as extending from the knob 261 through to the bottom so the wedge 251. An access groove 263 is carried by the leg 259 while An access groove 263 is carried by the leg 259 while an access groove 265 is carried by the leg 255.

Referring to FIG. 30, a sectional view taken along line 30-30 of FIG. 29 illustrates the use of a central support block 271 to support the a central threaded surface 273 and the legs 255 and 259.

Referring to FIG. 31, a view of a thin, inset hinge 281 utilizable with any of the obturators, but particularly obturators 33 and 241, is shown. In the case of obturator 33, by way of example, upper portions 53 accommodate control shaft 49 with its through bore 111. Inset hinge 281 may be implaced with an inset 283 and secured with machine screws 285. Inset hinge 281 may be made of a "living hinge" material such as a hard plastic, or it can have its operations base upon control bending of a pre-specified length of steel, since the angle of bend is slight. The connection between the upper portions 53 and the upper control housing 37 may be by any sort of interlocking mechanism, the aforementioned pivot blocks 59 or other mechanism.

Referring to FIG. 32, a sectional view of the obturator 33 within the working tube 35 is seen. The wedge 51 is seen at the bottom of the internal wedge conforming space 123. Once the spreading of the working tube 35 is accomplished the working tube 35 is kept open by any of the methods disclosed herein. Also seen is a pivot ball 116 to allow the control shaft 49 to turn with respect to the wedge. The pivot ball will continue to support a central aperture bore 111. Once the working tube 35 is stabilized in its open position, the obturator 33 is returned to its collapsed state as is shown in FIG. 33.

Figure 34:
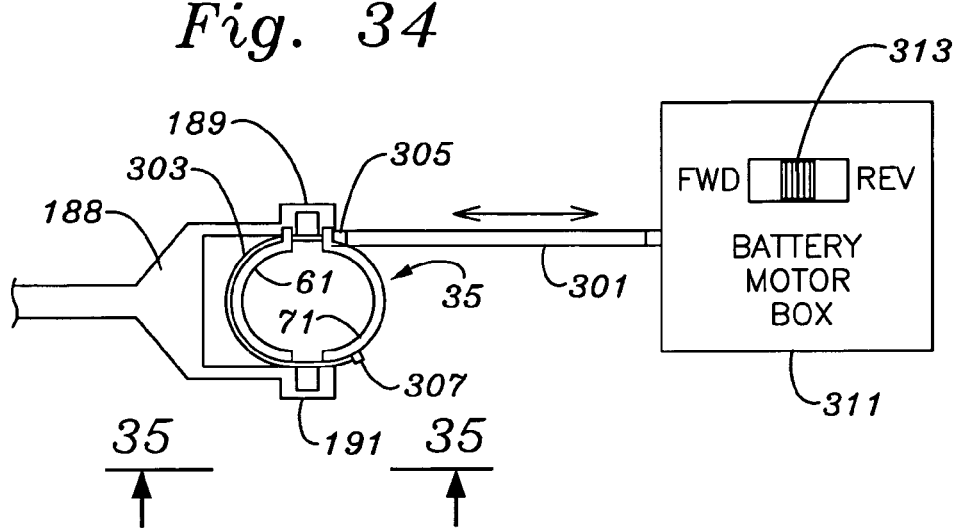
FIG. 34 illustrates a top and schematic view of the use of a remote power control to provide instant control of the working tube using an adjustable restriction on the upper angled hemicylindrical portions of the working tube.

Provision of electro-mechanical power to the operation of the working tube 35 can provide a surgeon an additional degree of instant control. Referring to FIG. 34, a top and schematic view of the use of a remote power control to provide instant control of the working tube 25, similar to the view seen in FIG. 25 illustrates the use of a remote annular control cable 301 using an internal cable 303 which is closely attached using a guide 305 and which circles the upper angled hemicylindrical portion 67 and 71, terminating at an end fitting 307.

The annular cable 301 is controlled by a BATTERY MOTOR BOX 311 having a forward and reverse switch 313 (with off or non actuation being the middle position). This enables the surgeon to expand the surgical field as needed and to collapse the surgical field to focus on certain working areas.

BATTERY MOTOR BOX 311 is configured with gears to cause the cable 303 to forcibly move axially within the annular cable 301 to transmit mechanical power to the working tube 35.

Figure 35:
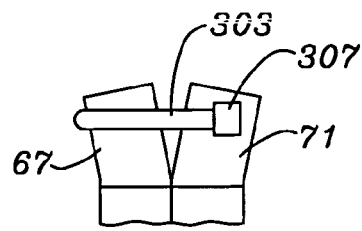
FIG. 35 is a view taken along line 35-35 of FIG. 34 and illustrating the method of attachment of the cable or band constriction.

Referring to FIG. 35, a view taken along line 35-35 of FIG. 34 illustrates how the cable 303 is held in place and a closeup of the end termination 307.

Figure 36:
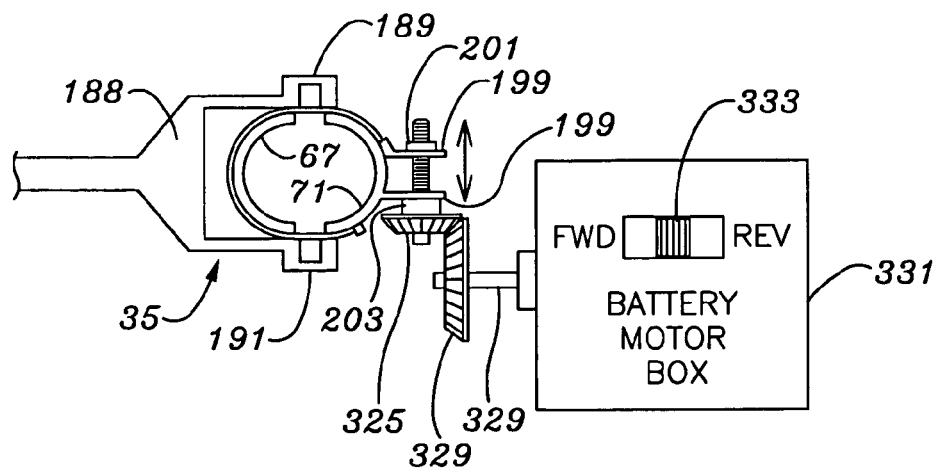
FIG. 36 is a mechanically operated version of the nut and bolt constriction band seen in FIG. 25.

Referring to FIG. 36, a mechanically operated version of the nut 201 and bolt 203 constriction band seen in FIG. 25. The mechanical power linkage can be provided remotely as by a rotating annular cable, but the basic mechanical setup shown illustrates the mechanical principles. On the bolt 203, a gear head 325 is implaced, either by attachment or by the provision of a threaded member and gear head made together. A second gear head 327 is utilized to show the possibility of providing a right angle power take-off in the event that the power connection interferes with the area around the surgical field. A shaft 329 extends from a BATTERY MOTOR BOX 331. The BATTERY MOTOR BOX 331 has a forward and reverse switch 333, (with off or non actuation being the middle position). Shaft 329 could be flexible and connected directly into axial alignment with the threaded member of bolt 201 or an integrally formed threaded member.

Advantages Over Existing Surgical Techniques

In terms of general advantages, there are differences between the minimal incision maximal access system 31, and its components as described in all of the drawings herein (but which will be referred throughout herein simply as the minimal incision maximal access system 31, or simply system 31) and other devices and procedures.

1. With regard to the Traditional microdiskectomy technique, the minimal incision maximal access system 31 allows for at least the same, if not better visualization access of the operative field. System 31 offers the same 3-Dimensional work ability or, if preferred, an endoscope can be utilized. System 31 minimizes muscle injury with spread versus extensive cautery dissection. System 31 has clear advantage on the challenging obese and very large patient where the traditional microdiskectomy technique is almost impossible to be applied.

2. With regard to open pedicle screw insertion procedures, system 31 offers muscle approach minimizing muscle devascularization and denervation. The traditional approach had required at least one level proximal and one level distal additional exposure causing extensive muscle injury often leading to "fibrotic" muscle changes resulting in chronic painful and stiff lower back syndrome. System 31 offers the most direct approach to the pedicle entry point selecting the avascular plane between the longissimus and multifidus muscles.

3. With regard to the Sextant Procedure, system 31 offers clear advantage over the Sextant procedure. First, the system 31 offers a procedure which is not a blind pedicle screw technique. System 31 can be applied to larger and more obese patients in which the Sextant procedure cannot be utilized. In this procedure using system 31 oosterolateral fusion can be performed along with insertion of the pedicle screws. The sextant procedure is strictly tension band stabilization.

In general, the components of the minimal incision maximal access system 31 are very simple the hemispherical shapes used for the working tube can be round or oval. A keying system can be held to align the obturator 33 to the working tube 35. In the case of an oval system, the alignment would be automatic.

The minimal incision maximal access system 31 is a modular system with interchangeable parts for both the working tube 35 and the obturator 33. The guide Pin 155 is of simple construction, as is the fascial incisor 169. The working tube 35 has a limited number of basic parts, and can be made in the simple, two main piece version of FIG. 28, or the multi-piece version of FIG. 1, which enables retractor-sleeve substitution. A hinge and stabilization mechanism completes the simplified construction.

The obturator 33 is also of simple construction, with upper control housing 37, pair of spreading legs 39 and 41, and an internal hinge, whether the pivot blocks 59 or hinge 281 and its ability to support a control shaft 49 having a bore 111 for a guide pin 155. Guide pin 155 may preferably have a size of from about 0.3 mm to 0.40 mm diameter and 30 cm to 40 cm in length. The fascial incisor may preferably be cannulated for usage with the guide pin 155 and have a width of about 2 mm more than the associated retractor. The overall cutting head length of about 1.2 cm has a shape as indicated in the pin 155.

The working tube 35 can have several variations and added details including the simplest shapes as dictated by intended usage. Working tube 35 can have a simple fluted hemitube shape or a Slanted box shape. Further, the possibility of a fluted oval shape is dictated when the approach is more angular. The working tube 35 can have an attachment for an endoscope. Working tube 35 can also have a non-symmetric appearance as by having longitudinal cross sectional shape with half of its shape being rounded and one half of its shape being rectangular or box shaped. This could also give rise to a similarly shaped obturator 33. The working tube 35 should have an anti-reflective inner coating and may be of modular construction.

The preferred lower dimensions for the lower tube hemicylindrical portions 65 and 69 include an overall shape which is semi tubular round or oval and having a width of from about 1.6-3.0 cm and a length of from about 4.0-18 cm. Hemicylindrical portions 65 and 69 may have custom cut outs depending upon planned application.

The hinge assembly 77 may have male-female post or male-female dial lock design, as well as a hinge housing and a bias (by spring or other mechanism) to keep angular displaceable portions of the working tube 35 closed a "universal" port provides a point of attachment of an endoscopic or stabilizer bar.

The obturator 33 may be any controlled opening device including a circular band or cable, force Plates, or a device attached to hinge assembly 77 or other hinge assembly.

All sleeve attachments including the attachable legs 39 and 41, as well as the lower tube hemicylindrical portions 65 and 69 should be of the friction grip type or snap and lock type or other suitable connection method or structure.

Obturator 215 may have squeeze grip scissor style handles 219 and 217 and a controlled dilator. It may utilize an enclosed design with a handle cover having a no-slip surface. It may be attached to the hinge housing of the working tube or separate hinge housing. In fact, it may be of a design to be held in place solely by the working tube 35. Ideally a cavity will be provided through the center axis to contain the shaft for the dilator mechanism if applicable.

The central bore 111 of the obturator 33 may have a diameter of from about 5-10 mm, depending upon the size of the obturator 33 utilized. Obturator 33 should be provided in various widths and length to match working tube. The working tips of the spreading legs 39 and 41 may be changeable according to surgical procedures as described in the operative procedures herein. It may have an inner chamber, or internal wedge conforming space 123 slanted in shape wider proximal and more narrow distal to accommodate the wedge 51. The internal wedge conforming space 123 can be enclosed with expanding contracting sleeve.

Other Procedures

Many other procedures can be facilitated with the use of the inventive minimal incision maximal access system 31 and methods practiced therewith. Procedure I, a diskectomy and nerve decompression procedure was described above with reference to the Figures. Other procedures are as follows:

Procedure II: Facet Fusion

1. Patient prone on Jackson Table with normal lordosis preserved. This can be increased by placing additional thigh and chest support to increase lumbar lordosis.
2. Insert percutaneous special guide pin perpendicular to the floor at a point 1 cm caudal to the Alar-Superior facet notch.
3. Apply a flag guide to a first guide pin 155 #1.
4. Measure skin to bone depth from the scale on guide pin 155 #1.
5. Slide drill guide mechanism on the flag guide to match the skin bone distance.
6. Insert guide pin 155 #2 through the drill guide to dock on the superior facet.
7. Make a small skin incision for the obturator 33.
8. Working tube 35 should be small oval or round with medial cutout to maximally medialize the working tube 35.
9. Advance the working tube 35 to the L5-S1 joint and dock.
10. Drill the guide pin across the joint medial to lateral, rostral to caudal. If in proper position, advance across the joint to engage the ala.
11. Drill across the joint with a cannulated drill.
12. Check depth flouroscopically and measure.
13. Pick appropriate screw length.
14. Insert specially designed facet screw and protective bracket, secure tightly.

Procedure III: Posterior Lumbar Interbody Fusion (PLIF)

1. First half of the procedure similar to microdiskectomy (Procedure I) except for the use of a larger diameter sized working tube 35. Use a 20-25 mm round or elliptical diameter working tube 35 with a medial cutout to allow docking as close to midline as possible.
2. Following diskectomy enlarge the laminotomy to accommodate the tools use for the specific PLIF such as Brantigan cage or Tangent.

Procedure IV: Transfacet Interbody Fusion (TFIF)

1. Follow the same procedure as the PLIF in terms of selecting and inserting the Working Tube 35.
2. Following the diskectomy, resect the facet joint.
3. Approach the posterolateral disc space through the medial ⅔ of the facet joint. Take care not to injure the exiting root above.
4. Proceed with Brantigan cage instruments and interbody cages.

Procedure V: Pedicle Screw Instrumentation Technique

1. Place the patient 151 Prone position on a Jackson Table.
2. Guide pin 155 is docked on facet joint angled 30 degree lateral to medial in the plane between the longissimus muscle longitudinally and multifidus muscle medially.
3. Make skin incision.
4. Fascial incisor introduction.
5. Introduce the obturator 33 working tube 35 assembly between the longissimus and multifidus and progressively open the obturator 33 tip ends of the legs 39 and 41, gradually reaching from the joint above and the joint below.

6. Advance the working tube 35 and retract the obturator 33.

7. Use the elliptical Working Tube size 2.5 cm wide and open up to 5 cm.

Procedure IV: Anterior Lateral Lumbar Diskectomy Fusion

1. Mid lateral decubitus position left side up. Place a "waist roll" to prevent sag of the mid lumbar spine.
2. Identify proper level of surgery fluoroscopically.
3. Insert a guide pin 155 #1 percutaneously into the superior facet perpendicular to the spine.
4. Measure depth skin to joint on the scaled guide pin 155 #1.
5. Insert cannulated flag guide over guide pin 155 #1.
6. Slide the drill guide to match the depth.
7. Insert a guide pin 155 #2 down to the disc space.
8. Make skin incision and insert fascial cover.
9. Insert the working tube 35 and Obturator 33 combination.
10. Progressively dilate the obturator 33.
11. Advance the working tube 35.
12. Perform anterolateral diskectomy and interbody fusion as taught above.
13. Use a round or oval shaped retractor or lower tube hemicylindrical portion 65 and 69 as inserts preferably with distal end cutouts in each.

Procedure VII: Posterior Cervical Foramenotomy and Lateral Mass Plating

1. The patient is placed in a prone position on a Jackson table.
2. Fluoroscopic identification of the level of surgery is had.
3. Percutaneously insert guide pin 155 with AP and lateral fluoroscopic views.
4. Make the initial skin incision.
5. Apply the working tube 35 with obturator 33 into the incision.
6. Perform slow dilation of the muscle.
7. Advance the working tube 35 and collapse and remove the obturator 33.
8. Proceed with surgery. Type of sleeve or lower tube hemicylindrical portion 65 should be round or oval with slanted and to match the slanted lamina.
9. For application for Lateral mass plating use an oval working tube 35 for a greater exposure.

Procedure VIII: Anterior Cervical Diskectomy Fusion

1. Begin with standard anterior cervical diskectomy fusion approach with a incision on the left or right side of the neck.
2. Blunt finger dissection is performed between the lateral vascular structures and the medial strap muscle and visceral structures down to the prevertebral fascia.
3. Establish the correct level to be operated on fluoroscopically and the guide pin 155 inserted into the disc.
4. Apply the working tube 35 and obturator 33 combination and dock at the proper level of the anterior spring.
5. Open the working tube 35 and obturator 33.
6. Mobilize longus colli muscle.
7. Use special Bent Homen Retractor specifically design to retract the longus colli.
8. Proceed with surgery.

Procedure IX: Anterior Lumbar Interbody Fusion

1. Begin with the standard approach whether it is retroperitoneal, transperitoneal or laparoscopic.
2. Apply the special anterior lumbar interbody fusion working tube 35 and obturator 33. This is a design with a medial lateral opening. It is oval shape and preferably with skirts 133 and 135. The distal end of the retractor sleeve is slightly flared outward to retract the vessels safely. There is a skirt 133 or 135 applied to the cephalad side and possibly to the caudal side.

3. With the vessels and the abdominal contents safely retracted out of harms way, proceed with diskectomy and fusion.

One of the aspects emphasized up to this point for the system 31 is structure and circumstance to minimize the upper entry point of the surgery while providing an expanded working area at the distal end of the tube. Structures which achieve this geometry have been shown, and include a flared upper end so that the aperture remains open regardless of the angle of spread.

In other applications it is permissible to expand the aperture opening at the top of the working sleeve assembly. Expansion can be for the purposes of introducing further working devices into the working tube, as well as to expand and protect the visual field. For example, further working devices may include implant tools and their held implants, tools to insert plates and screws, and tools to manipulate all of these into their final positions.

Visual field protection can be introduced where the surrounding tissue may tend to flow, move or obstruct the surgical working field. Where the bottom-most portions of the spread apart hemicylindrical tube are spread apart, tissue tends to enter the space between the bottom parts of the tube. Additional guarding structure needs to be introduced.

a description of the desired articulation of what is hereinafter referred to as a working tube assembly 417, and including the working tube hemicylindrical portions is begun with respect to FIG. 37. The designation of working tube assembly 417 refers to all of the tube structures seen in the earlier FIGS. 1-36 and as seen in any of the following Figures. FIG. 37 is an isolated view of two hemicylindrical tube sections shown joined in a tubular relationship and indicating at least a pair of pivot axes on each hemicylindrical tube section.

At the top of the structure shown in FIG. 37 a dashed line indicates an optional fluted structure 419. Fluted structure is omitted from the drawings for FIGS. 37-49 in order that the views from the top will not be obscured. The optional fluted opening 419 and is often employed both to maintain the visual field upon opening, as well as to make it easier to add instrumentation into the surgical field. This structure is recommended, as well as all reasonable accommodation to facilitate its use.

a first hemicylindrical tube 421 is shown in alignment with a second hemicylindrical tube 423. Rather than having the upper ends flared out to maintain a circular visual field on a full open position, a clearance notch 425 is provided in first hemicylindrical tube 421, while a clearance notch 427 is provided in second hemicylindrical tube 423.

The lowermost extent of the clearance notches 425 and 427 coincide with an upper pivot axis 431 of first hemicylindrical tube 421 and upper pivot axis 433 of first hemicylindrical tube 421. The pivot axes 431 and 433 may include supports either derived from structures going into or out of the first and second hemicylindrical tubes 421 and 423. In the view of FIGS. 37-39, the structures seen facing the viewer are repeated on the opposite side. Thus, pivot axes 431 and 433 are also located on the side opposite that seen in FIGS. 37-39. The same is true for all of the numbered structures. In this position, the simultaneous pivoting about the pivot axes 431 and 433 of the first and second hemicylindrical tubes 421 and 423 will not cause interference by portions of the first and second hemicylindrical tubes 421 and 423 which would otherwise interfere.

Further, a lower pivot axis 435 is provided below the upper pivot axis 431 of first hemicylindrical tube 421. Similarly, a lower pivot axis 437 is provided below the upper pivot axis 433 of second hemicylindrical tube 423. The geometry and pivot points having been identified, double headed arrows illustrate that the pivot points should be able to move toward and away from each other. Ideally, the only limitation should be the interference from the lower ends of the first and second hemicylindrical tubes 421 and 423 with each other. Where the mechanism for moving the first and second hemicylindrical tubes 421 and 423 has maximum independence, secondary considerations of interference are eliminated and only the primary interference between the first and second hemicylindrical tubes 421 and 423 will remain. Where the control mechanism for movement is lesser than that which allows maximum independence, savings can be had in terms of complexity of the mechanism at the expense of the freedom of movement.

FIG. 37 illustrates the first and second hemicylindrical tubes 421 and 423 in a closely aligned relationship where the upper pivot axis 431 is closest to the upper pivot axis 433 and where the lower pivot axis 435 is closest to the lower pivot axis 437. This is the position expected to be used for entry into the body of the patient, especially along with a guide (to be shown) which will be located within and extending below the assembled and parallel linear tube formed by first and second hemicylindrical tubes 421 and 423 to provide a reduced insertion resistance.

Ideally, the first and second hemicylindrical tubes 421 and 423 will be inserted as shown in FIG. 37 and then manipulated to a position shown in FIG. 38. FIG. 38 is an isolated view of two hemicylindrical tube sections as seen in FIG. 38 which are angularly displaced apart about a shared first pivot axis on each of the hemicylindrical tube sections. The position in FIG. 38 is characterized by the fact that upper pivot axes 431 and 433 have the same separation as seen in FIG. 37, but in which the lower pivot axes 435 and 437 have moved apart. The position seen in FIG. 38 will be likely achieved just after insertion and in which the internal tissues have been pushed apart. Depending upon the surgical procedure, the first and second hemicylindrical tubes 421 and 423 will be chosen based upon length, so that the lower end will be at the correct height for the tissues to be viewed, manipulated and treated. The action can continue until the lower ends of the first and second hemicylindrical tubes 421 and 423 are sufficiently spaced apart for view and manipulation of the tissues between and adjacent the lower ends. If there is a sufficient viewing opening based upon the original distance of separation of the upper pivot axes 431 and 433, the procedure may continue through an aperture about the same size of the tube shape seen in FIG. 37.

Where more of an opening is needed, the first and second hemicylindrical tubes 421 and 423 upper pivot axes 431 and 433 can move more widely apart until a position such as that seen in FIG. 39 is achieved. FIG. 39 is an isolated view of the two first and second hemicylindrical tubes 421 and 423 which are angularly displaced apart about a shared second pivot axis on each of the hemicylindrical tube sections. It should be emphasized that the position seen in FIG. 39 is a position where both the first and second hemicylindrical tubes 421 and 423 are parallel and separated from each other, but this need not be the case. From the position seen in FIG. 38, the upper pivot axes 431 and 433 can be moved apart from each other while the lower pivot axes 435 and 437 either remain a constant distance from each other or are brought together. This range of articulation described can be used to physically manipulates the tissues in contact with the first and second hemicylindrical tubes 421 and 423 for any number of reasons, including introduction of further instruments if necessary, as well as to react to changing conditions of tissue at the lower tube.

In both FIGS. 38 and 39 a pair of opposing edges 439 can be utilized to support structures introduced between the first and second hemicylindrical tubes 421 and 423. Other structures can be used including depressions, apertures and internal projections, such as hooks or latches. An internal structure within the first and second hemicylindrical tubes 421 and 423 would pose little risk of nick to the patient and can be designed to do nothing more than have a minimal interference effect with respect to the visual field.

As will be shown, a number of external structures can be employed to achieve the relative separation positions of the upper pivot axes 431 and 433, as well as the lower pivot axes 435 and 437 that nearly any type of angle can exist on either side of a parallel relationship between the first and second hemicylindrical tubes 421 and 423, but that most will be in a range of from a parallel relationship to some form of angular relationship seen in FIG. 38, where the upper ends at the clearance notches 425 and 427 are closer together than the lower ends distal to the upper pivot axes 431 and 433 and lower pivot axes 435 and 437.

One example of a side shield 441 is seen in FIG. 40. FIG. 40 is a plan view of a given width supplemental side shield 441 having a width of approximately the separation of the hemicylindrical tube sections as seen in FIG. 39, while accompanying FIG. 41 is a top view of the supplemental side shield 441 of FIG. 40 emphasizing its shape. The side shield 441 can be of any shape, but is shown in a rectangular shape to correspond with the first and second hemicylindrical tubes 421 and 423 in a parallel position as seen in FIG. 39. The side shield 441 has a main portion which includes a first side 443 and a pair of lateral engagement portions 445. The side shield 441 can depend from a number of other structures, but the side shield 441 seen in FIGS. 40 and 41 utilize an offset surfaces as engagement portions 445. This geometry, will, absent any interfering structures which are attached to manipulate the first and second hemicylindrical tubes 421 and 423, enable the side shield 441 to be introduced linearly from the top of first and second hemicylindrical tubes 421 and 423. The introduction of side shield 441 may be guided somewhat into engagement by the clearance etches 425 and 427. Much smaller engagement portions 445 could be used to engage the outer edges 439 of the first and second hemicylindrical tubes 421 and 423, so long as the orientation is so as to protect the surrounding tissues. FIG. 41 emphasizes the geometry and shows a second side 447.

In the orinetation shown, the second side 447 would face toward the inside of the general tube formed in the orientation of FIG. 39. If two of the side shields 441 were used, one on either side of the opening seen in FIG. 39, the tube shape would be closed on both sides, and an oval viewing area would be formed. It should be emphasized that the side shield 441 can depend from any structure, and not just the opposing edges 439 seen in FIG. 39. Structure used to manipulate the first and second hemicylindrical tubes 421 and 423 can be used to both guide and secure any side shield 443.

In terms of a structure to manipulate the first and second hemicylindrical tubes 421 and 423, it is preferable that the upper pivot axes 431 and 433 may be urged toward and away from each other independently of the urging of the lower pivot axes 435 and 437 toward and away from each other independently a mechanism which would prevent all manipulations of the first and second hemicylindrical tubes 421 and 423 to a position of binding is desirable, but its complexity may obstruct the surgical field. For example, it would be good to have a mechanism which would prevent upper pivot axes 431 and 433 from moving away from each other while the lower pivot axes 425 and 437 are in their close proximity as depicted in FIG. 37. In some cases operator knowledge and skill will probably be required.

In terms of supporting the upper pivot axes 431 and 433 and lower pivot axes 425 and 437, the pivoting and movement may be passive with mechanisms to push or pull directly on the first and second hemicylindrical tubes 421 and 423 or structures which are mechanically attached. As an example of the use of force and movement urging at the pivot points, FIG. 42 illustrates one such system as a pivoting thread support system 551. The gearing is shown as unduly expansive to illustrate simply the action, but in reality, several gears may be used.

Further, since the a pivoting thread support system 551 is viewed from the top, and as operating the upper pivot axes 431 and 433, a similar arrangement would be used for the lower pivot axes 425 and 437. a set of four pivot fittings 553 provide a threaded interior spaced apart from the first and second hemicylindrical tubes 421 and 423, or fittings supporting the first and second hemicylindrical tubes 421 and 423. The fittings 553 enable the first and second hemicylindrical tubes 421 and 423 to tilt while keeping the threaded apertures in alignment.

a first threaded member 555 has a pair of threaded areas in which the threads are oppose pitched. The threads engaging the fitting 553 of first hemicylindrical tube 421 are set to urge first hemicylindrical tube 421 away from second hemicylindrical tube 423, at the same time that the same turning of the first threaded member engages fitting 553 of first hemicylindrical tube 423 set to urge first hemicylindrical tube 423 away from second hemicylindrical tube 421. This means that the turning of first threaded member 555 in one direction urges the first and second hemicylindrical tubes 421 and 423 evenly away from each other, and alternatively, the turning of first threaded member 555 in the opposite direction urges the first and second hemicylindrical tubes 421 and 423 evenly toward each other.

Likewise, a second threaded member 557 has a pair of threaded areas in which the threads are oppose pitched. The threads engaging the fitting 553 of first hemicylindrical tube 421 are set to urge first hemicylindrical tube 421 away from second hemicylindrical tube 423, at the same time that the same turning of the first threaded member engages fitting 553 of first hemicylindrical tube 423 set to urge first hemicylindrical tube 423 away from second hemicylindrical tube 421, but in an oppose orientation than the threads of first threaded member 555. This means that the turning of second threaded member 557 in the other direction (while the first threaded member 555 is turned in a first direction) urges the first and second hemicylindrical tubes 421 and 423 evenly away from each other. a pair of over sized gears, including a first gear 559 associated with the first threaded member 555, and a second gear 561 associated with the second threaded member 557 act to cause the first and second threaded members 555 and 557 to move simultaneously and oppositely. a knob 563 is used to manipulate both the first gear 559, which manipulates the second gear 561. In a realization in which more gears 559 and 561 are provided, the size of the gears can be reduced and for each intermediate gear, the sense of the threaded members 555 and 557 will change from opposite to same.

Referring to FIG. 43, a surrounding frame system 571 is seen which is utilized to provide and enable pivoting and translation. A surrounding frame 573 has an open slot 575 which accommodates a pair of pins 577 and 579 which preferably have some tracking along the slot 575 to insure that neither the first hemicylindrical tube 421 nor the second hemicylindrical tube 423 are able to turn within the frame 573. The opposite side of the frame 573 will have a similar slot 575. However, where the structures which engage the slot are especially over sized, or where the structural integrity is sufficient, only one slot need be used. The structural dependence on the frame 573 should be such that the two opposing first and second hemicylindrical tubes 421 and 423 will always oppose each other and cannot twist away from each other and can only pivot along their long axis.

a turn fitting 581 enables a threaded member 583 to turn while being axially fixed to the first hemicylindrical tube 421. The threaded member 583 may be threadably engaged to an internal thread 585 at the end of the frame 573. In this case a knob 587 is used to manually turn the threaded member 583 independently to move the first hemicylindrical tube 421 to the left or to the right. A turn fitting is a structure which holds the end of the threaded member and allows the threaded member 583 to urge the fitting forward or backward while continuing to turn.

In the alternative, knob 587 may have an internal thread, and turned with respect to the threaded member 583 draw the threaded member out of the frame 573. In this case, a spring (as will be shown) could be used to help reverse this operation. Where the knob 587 is internally threaded, the end of the threaded member may be fixed directly to its first hemicylindrical tube 421.

In sum, there are three ways to affect motion, preferably the internal threads 585 enable the threaded member 583 to turn to urge first hemicylindrical tube 421 in both directions with respect to the frame 573. In the alternative, the threaded member 583 may act only to urge the first hemicylindrical tube 421, and the tubes 421 and 423 may have another mechanism urging them apart or simply move apart based upon other forces or other structures present. Third, the threaded member 583 may have an end anchored to the first hemicylindrical tube 421 with an internally threaded surface inside knob 587 to enable the knob 587 to be turned to cause the length of threaded member 583 to be withdrawn from the frame 583. A spring, or other fitting can be used to help reverse the direction of travel. All of the knobs and threaded members shown hereafter have the ability for all three modes of action.

Similarly, a turn fitting 591 enables a threaded member 593 to turn while being axially fixed to the second hemicylindrical tube 423. The threaded member 593 threadably engaged to an internal thread 595 at the end of the frame 573. a knob 597 is used to manually turn the threaded member 593 independently to move the second hemicylindrical tube 423 to the left or to the right.

Similarly, a second surrounding frame 573 has an open slot 575 which accommodates a pair of pins 601 and 603 having expanded heads which fit outside the slot 575 to provide tracking along the slot 575 to further insure that neither the first hemicylindrical tube 421 nor the second hemicylindrical tube 423 are able to turn within either of the frames 573.

a turn fitting 611 enables a threaded member 613 to turn while being axially fixed to the first hemicylindrical tube 421. The threaded member 613 is threadably engaged to an internal thread 615 at the end of the frame 573. a knob 617 is used to manually turn the threaded member 613 independently to move the first hemicylindrical tube 421, at its lower pivot axis 435 at the center of the pin 601. Similarly, a turn fitting 621 enables a threaded member 623 to turn while being axially fixed to the second hemicylindrical tube 423. The threaded member 623 threadably engaged to an internal thread 625 at the end of the lower located frame 573. a knob 627 is used to manually turn the threaded member 623 independently to move the second hemicylindrical tube 423 to the left or to the right at its lower pivot axis 437 at the center of the pin 603.

With the configuration of FIG. 43, the position within the upper located frame 573 and separation of the pivot axes 431 and 433 (represented by the pins 577 and 589) can be exactly specified. Likewise, the position within the lower located frame 573 and separation of the pivot axes 435 and 437 (represented by the pins 601 and 603) can be exactly specified. In typical use, the knobs 617 and 627 and will be activated after insertion to achieve the configuration seen in FIG. 38, and then followed by the use of the knobs 587 and 597 to achieve the configuration seen in FIG. 39, if necessary. Thereupon the optional side shield 441 may be employed. Where a lesser separation than that seen in FIG. 39 is used, a narrower side shield 441 may be employed. In a surgical kit, several such shields 441 of different size and shape may be available.

Referring to FIG. 44, a view looking down into the structure of FIG. 43 shows the overall orientation and further illustrates an optional securing tang 629 which may be used with either of the upper located or lower located frame 573, and may be located in any position, or extended in any direction, to better enable the surgeon to stabilize and manipulate any of the assemblies 417, 551 and 571 seen. Any structure can be used to help secure the frame 573 and or the first and second hemicylindrical tubes 421 and 423. FIG. 44 is an equivalent view through the lower of the frames 573, including the knobs 617 and 627 as the two frames 573 have equivalent action. Note that having complete control over both the separation, angular relationship, and position of the first and second hemicylindrical tubes 421 and 423 within the frame 573 will enable the surgical practitioner to position the line of sight of the working tube along the frame 573 length and to generally have complete control.

Also shown in FIG. 44 is an optional spring 630 which can be used to bias the force acting upon either of the first and second hemicylindrical tubes 421 and 423, or it can be used to bias a knob 597 away from the frame 573. Although shown as an option, the use of a spring 639 may contribute significantly where force is to be had in one direction only, as well as to lock a threaded member such as 593 into a turn fitting by keeping a pulling bias in place.

In some cases it may be desired to reduce the number of controls to accomplish certain objectives, such as simplicity, less controllability, less moving parts, inexpense, or the critical need for space about the upper part of any of the assemblies 417, 551 and 571. One example of an arrangement is seen in FIG. 45. a frame 631 has an interior having one surface which may generally match one of the first and second hemicylindrical tubes 421 and 423, and in this case first hemicylindrical tube 421. The frame 631 may be attached to the first hemicylindrical tube 421 by tack welding or the like, or other means. a single threaded member 633 includes a knob 635. a structure 637 can be either an engagement turning block to enable the threaded member 633 to both push and pull on the second hemicylindrical tube 423, or it may simply be a wear block to allow the threaded member 633 to push against it and to protect the second hemicylindrical tube 423 from wear.

Because half of the tube assembly of first and second hemicylindrical tubes 421 and 423 is supported by the frame 631, the second hemicylindrical tube 423 is left to move only slightly and assuming that FIG. 45 is an upper view and that the pivoting of the second hemicylindrical tube 423 is accomplished at a lower level, especially at the level of lower pivot axis 437, the frame 631 is left to control second hemicylindrical tube 423 by simply pushing, or by pushing and pulling. Where structure 637 is a turning block, there is a bulbous expansion at the end of threaded member 633 which snaps into structure 637 as a turning block and is free to turn and both push and pull second hemicylindrical tube 423. The threaded member 633 is threadably engaged into an internal threaded bore 639 within the frame 631.

Referring to FIG. 46, one embodiment of a manipulative structure which works well with the structure of FIG. 45 is shown. The structure shown is a partial section taken at the lower pivot axis level and includes means for pushing and pulling, or pushing alone. Preferably, when used with the structure of FIG. 45, it will include pushing and pulling, especially if the structure of FIG. 45 performs pushing alone. Either of the structures in FIG. 43 at either the upper or lower pivot axis levels can be substituted for either of the structures shown in FIGS. 45 and 46 as the structures in FIG. 43 provide both pushing, pulling, pivoting and level support.

Where the structures of FIG. 45 provides both pushing and pulling, it can be used along with a second structures at the lower pivot axis as any structure which provides both pushing and pulling will also provide some pivoting support. Further, the structure shown in FIG. 46 is hinged to provide additional pivoting support. The structure of FIG. 46 can be used at either the upper pivot axes 431 and 433 or the lower pivot axes 435 and 437. Both the structures of FIGS. 45 and 46 demonstrate clearly that lesser control structures than are shown in FIG. 43 can be used to control the first and second hemicylindrical tubes 421 and 423, along with lesser control inputs, and less control specificity, but also with less moving parts and a lesser mechanical complexity.

Referring again to FIG. 46, second hemicylindrical tube 423 is seen as tack welded to a reinforcement 651. The purpose of reinforcement 651 is to provide an expanded thickness of material so that pivoting can occur closer to the edge 439 as is possible. It is further possible to continue the extent of the reinforcement 651 and its pivot point in the direction of first hemicylindrical tube 421 if the other geometries of the other components permit. Reinforcement 651 contains a pair of threaded bores 653, each of which accommodates one of the threaded screws or bolts 655 shown. The bolts 655 each extend through one end of a "U" shaped fitting 657, so that the reinforcement 651 and attached second hemicylindrical tube 423 pivots with respect to the fitting 657. a threaded member 659 engaged an internal threaded bore 671, and has a knob 673 for ease of manual operation.

The threaded member is connected to a turn fitting 675 the first hemicylindrical tubes 421 to be moved toward and away from second hemicylindrical tube 423. The use of the structure of FIGS. 45 and 46 may be used together to give the ability to provide control, although not as much control as is seen in FIG. 43. Also seen is an Referring to FIG. 47, another possible realization is seen, combining the control mechanisms of selected portions of FIGS. 37-46, combined with other possible options. An open frame system 691 is seen as having a frame 693 which is either open on at least one side, or which has a side expanded to a distance sufficient to introduce other structures to expand in that direction. Some of the components previously seen include pins 577 and 579 extending through slot 575. Pins 577 and 579 may have extended vertical and horizontal extent to garner additional stability from the frame 693, especially where one side is open.

Other structures may be used to insure that neither the first hemicylindrical tube 421 nor the second hemicylindrical tube 423 are able to turn within the frame 573. Also seen are turn fitting 581, threaded member 583, knob 587, turn fitting 591, threaded member 593, and knob 597. The view of FIG. 47 is from above, and thus the structures most closely correspond to the upper structures seen in FIG. 43 and in FIG. 44.

As can be seen in FIG. 47, a four point retractor system can be formed with the components and structures of the foregoing Figures. The first and second hemicylindrical tubes 421 and 423 are shown in the open position. On the longer connector arm of the frame 693, a side shield 695 is supported. The side shield 695 can derive its ability to hold tissue out of the visual field by being locked down onto the frame 693 in the same manner as a wrench fits a bolt head. In this configuration, the side shield can be inserted into the center of the surgical field and then rotated into position and moved down slightly to lock it into place. On the opposite side from side shield 695 is a retractor 697 which has a flat portion entering the surgical field and which is controlled from a point remote with respect to open frame system 691. An angled portion 699 turns from the flat portion seen entering the surgical field and extends down into the area between the open first and second hemicylindrical tubes 421 and 423.

Also seen are a series of small circular structures 701 about the peripheral upper surface of first and second hemicylindrical tubes 421 and 423. These structures are at least one of embedded fiber optics and ports for accepting fiber optics. The apertures formed in the metal open at a slight angle to the inside of the first and second hemicylindrical tubes 421 and 423 to direct light into the surgical field without producing a back reflection or other scatter. In cases where the fiber optic is permanently affixed, a light ring section can simply be snapped to or placed on the first and second hemicylindrical tubes 421 and 423. In cases where the apertures are provided, surgery can continue without fiber optics, or a fiber optics set can be added which can range from an illuminated ring (relying on low angle of incidence and snells law) to direct light through the openings which open to the inside of the first and second hemicylindrical tubes 421 and 423 at a low angle of incidence. Intermediary solutions, such as a light ring having a series of short fiber optic members for insertion into the apertures can be used. To facilitate the use of fiber optics, the hemicylindrical tubes 421 and 423 may be made from a composite material in which the fiber optic components may be present during formation of the tube structures. Other material may be used for tubes 421 and 423, including materials that either transmit light or have portions which transmit light.

As an alternative to the three sided frame 693, the open portion of the frame could be enclosed by an expandable member 703 which can have any manner of inerlock with the three sided frame 693. One such interlock is illustrated as simply an annular piston dependence where the expandable member 703 includes a smaller tubular insert 705 which fits closely into a matching bore 707 seen in the terminal ends of the three sided frame 693. The expandable member 703 can be used to lend additional support to the three sided frame 693, especially forces produced by the threaded members 583 and 593. The expandable member 703 is also useful to help support the retractor 697 where such provision is made. The main purpose of expandable member 703 is the adjustability to give greater clearance and access. The same adjustability could be had on the side three sided frame 693 which supports side shield 695, especially with a more complex mechanism to enable the frame expansion to be locked into place. A locking mechanism for expandable member 703 is not shown so that the drawings may be simplified, but lockability can be achieved in the same manner as any metal to metal frame construction known in any field of art.

Referring to FIG. 48, a side view of the side shield 695 is seen. The clearance for locking onto the frame 693 is about the same as the width of the frame 693 so that non rotational fixation can be transmitted along the length of the side shield 695.

Referring to FIG. 49, one possible configuration is seen for a variable depth guide 711 which is utilizable with any of the devices seen in FIGS. 37-46 or any other tubular, minimally invasive system. Variable depth guide 711 has a handle 713 controlling a shaft 715. Shaft 715 has a through bore 717 which is used to insert a guide line or guide pin to help insert any minimal access system seen in the earlier Figures.

a translatable detent ring 719 interacts with a series of detent indentations 721. The position of the detent ring 719 will correspond to the lengths of the first and second hemicylindrical tubes 421 and 423 with which the variable depth guide 711 is used. Once the practitioner inserts the variable depth guide 711 into any assembly containing a first and second hemicylindrical tubes 421 and 423, the necessary height can be adjusted so that the tip of the variable depth guide 711 extends just beyond the lower extent of the joined first and second hemicylindrical tubes 421 and 423. The height is adjusted by forcing the detent ring 719 to the proper detent indentation 721, and then inserting it into a closely associated first and second hemicylindrical tubes 421 and 423 to form an overall bullet shape for insertion, preferably a guide pin 155. Once inserted, the variable depth guide 711 is removed. The detent ring 719 carries a frusto-conical surface 723 where it is used with first and second hemicylindrical tubes 421 and 423 having fluted top areas as seen in FIG. 37 and in previous figures. Any mechanism can be used to achieve a detent action, including an internal pressure ring or a spring loaded bar, or protruding ball bearings. The positional stability of the detent ring can be specified by the spring action of the detent member, and should be sufficiently stable to enable deliberate manual fixation with no inadvertent movement occurring even where significant resistance is encountered.

While the present system 31 has been described in terms of a system of instruments and procedures for facilitating the performance of a microscopic lumbar diskectomy procedure, one skilled in the art will realize that the structure and techniques of the present system 31 can be applied to many appliances including any appliance which utilizes the embodiments of the instrumentation of the system 31 or any process which utilizes the steps of the system 31.

Although the system 31 has been derived with reference to particular illustrative embodiments thereof, many changes and modifications of the system 31 may become apparent to those skilled in the art without departing from the spirit and scope of the system 31. Therefore, included within the patent warranted hereon are all such changes and modifications as may reasonably and properly be included within the scope of this contribution to the art.

What is claimed:

1. A minimal incision maximal access working tube assembly comprising:
   a first hemicylindrical member having at least a first upper pivot axis nearer a proximal end of said first hemicylindrical member and at least a first lower pivot axis nearer a distal end of said first hemicylindrical member;
   a second hemicylindrical member having at least a first upper pivot axis nearer a proximal end of said second hemicylindrical member and at least a first lower pivot axis nearer a distal end of said second hemicylindrical member, and oriented with respect to said first hemicylindrical member to form a tube shape when brought into close proximity to said first hemicylindrical member;

a controllable support having an upper support and a lower support, each of the upper and lower supports allowing independent translation of the respective upper pivot axes and lower pivot axes with respect to the pivot axes of the other support.

2. The minimal incision maximal access working tube assembly as recited in claim 1 wherein said upper support is operable independently of said lower support.

3. The minimal incision maximal access working tube assembly as recited in claim 1 wherein said first and second hemicylindrical members define a chamfered proximal end.

4. The minimal incision maximal access working tube assembly as recited in claim 1 wherein said first and second hemicylindrical members are interchangeable.

5. The minimal incision maximal access working tube assembly as recited in claim 1 wherein said first and second hemicylindrical members further each comprise a first and second upper protrusion.

6. The minimal incision maximal access working tube assembly as recited in claim 5 wherein said upper support defining two slots therein, each slot being configured to accept one of said first and second upper protrusions.

7. The minimal incision maximal access working tube assembly as recited in claim 1 wherein said first and second hemicylindrical members further each comprise a first and second lower protrusion.

8. The minimal incision maximal access working tube assembly as recited in claim 7 wherein said lower support defining two slots therein, each slot being configured to accept one of said first and second upper protrusions.

9. The minimal incision maximal access working tube assembly as recited in claim 1 further comprising at least a threaded member and first and second pivot fittings on said first and second hemicylindrical members, respectively, said threaded member engaging at least one of said first and second pivot fittings, such that rotation of said threaded member urges one of first and second pivot fittings away from the other pivot fitting.

10. The minimal incision maximal access working tube assembly as recited in claim 9, wherein said threaded member includes a first threaded portion and a second threaded portion, said first and second threaded portions engaging said first and second pivot fittings, respectively, said first and second threaded portions having threads in opposite directions, such that rotation of said threaded member urges said first and second pivot fittings away from each other.

* * * * *